(12) United States Patent
Young-Dixon et al.

(10) Patent No.: US 12,109,418 B2
(45) Date of Patent: Oct. 8, 2024

(54) SEGMENTED LEAD INDEPENDENT ELECTRODE CONTROL FOR SENSING OR ADAPTIVE STIMULATION

(71) Applicant: Medtronic, Inc., Minneapolis, MN (US)

(72) Inventors: Brendan J. Young-Dixon, St. Paul, MN (US); Thomas L Chouinard, Maple Grove, MN (US); Lance Beall, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 289 days.

(21) Appl. No.: 17/522,612

(22) Filed: Nov. 9, 2021

(65) Prior Publication Data

US 2022/0161034 A1    May 26, 2022

Related U.S. Application Data

(60) Provisional application No. 63/118,470, filed on Nov. 25, 2020.

(51) Int. Cl.
*A61N 1/05* (2006.01)
*A61N 1/36* (2006.01)

(52) U.S. Cl.
CPC ....... *A61N 1/36185* (2013.01); *A61N 1/0534* (2013.01); *A61N 1/3606* (2013.01); *A61N 1/36139* (2013.01)

(58) Field of Classification Search
CPC .............. A61N 1/36185; A61N 1/0534; A61N 1/3606; A61N 1/36139; A61N 1/0529;
(Continued)

(56) References Cited

U.S. PATENT DOCUMENTS

| 4,592,359 A | 6/1986 | Galbraith |
| 4,931,795 A | 6/1990 | Gord |

(Continued)

FOREIGN PATENT DOCUMENTS

| EP | 2039391 A1 | 3/2009 |
| WO | 2001054579 A1 | 8/2001 |

(Continued)

OTHER PUBLICATIONS

Response to Extended Search Report dated Apr. 22, 2022, from counterpart European Application No. 21210495.4 filed Nov. 25, 2022, 16 pp.

(Continued)

*Primary Examiner* — Ankit D Tejani
*Assistant Examiner* — Joshua Brendon Solomon
(74) *Attorney, Agent, or Firm* — Shumaker & Sieffert, P.A.

(57) ABSTRACT

An example system includes a lead including a first electrode disposed at a first level, a second electrode disposed at a second level, a first group of segmented electrodes disposed at a third level, and a second group of segmented electrodes disposed at a fourth level. The example system also includes a medical device configured to deliver symmetrical electrical stimulation to a patient via the first group of segmented electrodes and the second group of segmented electrodes and sense a response to the stimulation via the first electrode and the second electrode.

20 Claims, 8 Drawing Sheets

(58) Field of Classification Search
CPC .............. A61N 1/3605; A61N 1/36121; A61N 1/37217; A61N 1/37282
See application file for complete search history.

(56) References Cited

U.S. PATENT DOCUMENTS

| | | | |
|---|---|---|---|
| 5,190,035 A | 3/1993 | Salo et al. | |
| 5,241,472 A | 8/1993 | Gur et al. | |
| 5,501,703 A | 3/1996 | Holsheimer et al. | |
| 5,713,922 A | 2/1998 | King | |
| 5,776,172 A | 7/1998 | Schulman et al. | |
| 5,800,465 A | 9/1998 | Thompson et al. | |
| 5,895,416 A | 4/1999 | Barreras, Sr. et al. | |
| 5,916,238 A | 6/1999 | Hauser et al. | |
| 5,954,758 A | 9/1999 | Peckham et al. | |
| 6,341,234 B1 | 2/2002 | Thong et al. | |
| 6,393,325 B1 | 5/2002 | Mann et al. | |
| 6,421,564 B1 | 7/2002 | Yerich et al. | |
| 6,505,078 B1 | 1/2003 | King et al. | |
| 6,516,227 B1 | 2/2003 | Meadows et al. | |
| 6,587,724 B2 | 7/2003 | Mann | |
| 6,609,032 B1 | 8/2003 | Woods et al. | |
| 6,625,482 B1 | 9/2003 | Panescu et al. | |
| 6,799,070 B2 | 9/2004 | Wolfe et al. | |
| 6,853,863 B2 | 2/2005 | Carter et al. | |
| 6,895,280 B2 | 5/2005 | Meadows et al. | |
| 6,909,917 B2 | 6/2005 | Woods et al. | |
| 7,035,690 B2 | 4/2006 | Goetz | |
| 7,127,297 B2 | 10/2006 | Law et al. | |
| 7,174,210 B1 | 2/2007 | Levine | |
| 7,180,760 B2 | 2/2007 | Varrichio et al. | |
| 7,216,001 B2 | 5/2007 | Hacker et al. | |
| 7,251,529 B2 | 7/2007 | Greenwood-Van Meerveld | |
| 7,271,663 B2 | 9/2007 | Baum et al. | |
| 7,317,948 B1 | 1/2008 | King et al. | |
| 7,386,348 B2 | 6/2008 | North et al. | |
| 7,387,603 B2 | 6/2008 | Gross et al. | |
| 7,389,147 B2 | 6/2008 | Wahlstrand et al. | |
| 7,463,928 B2 | 12/2008 | Lee et al. | |
| 7,477,723 B2 | 1/2009 | Kamegawa et al. | |
| 7,505,809 B2 | 3/2009 | Strommer et al. | |
| 7,519,428 B1 | 4/2009 | Palmer | |
| 7,519,431 B2 | 4/2009 | Goetz et al. | |
| 7,522,962 B1 | 4/2009 | Doron et al. | |
| 7,526,341 B2 | 4/2009 | Goetz et al. | |
| 7,567,834 B2 | 7/2009 | Clayton et al. | |
| 7,571,007 B2 | 8/2009 | Erickson et al. | |
| 7,623,918 B2 | 11/2009 | Goetz | |
| 7,768,151 B2 | 8/2010 | Andreu et al. | |
| 7,974,697 B2 | 7/2011 | Maschino et al. | |
| 8,055,337 B2 | 11/2011 | Moffitt et al. | |
| 8,560,080 B2 | 10/2013 | Goetz et al. | |
| 8,738,145 B2 | 5/2014 | Goetz et al. | |
| 8,825,169 B2 | 9/2014 | Zhu et al. | |
| 8,996,123 B2 | 3/2015 | Goetz et al. | |
| 9,358,390 B2 | 6/2016 | Polefko et al. | |
| 9,913,975 B2 | 3/2018 | Carbunaru et al. | |
| 10,199,125 B2 | 2/2019 | Rao et al. | |
| 2004/0059395 A1 | 3/2004 | North et al. | |
| 2004/0098063 A1 | 5/2004 | Goetz | |
| 2004/0210273 A1 | 10/2004 | Wang | |
| 2004/0267330 A1 | 12/2004 | Lee et al. | |
| 2005/0065556 A1 | 3/2005 | Reghabi et al. | |
| 2005/0131464 A1 | 6/2005 | Heinrich et al. | |
| 2006/0178706 A1 | 8/2006 | Lisogurski et al. | |
| 2006/0195145 A1 | 8/2006 | Lee et al. | |
| 2006/0229687 A1 | 10/2006 | Goetz et al. | |
| 2006/0241720 A1 | 10/2006 | Woods et al. | |
| 2006/0259079 A1 | 11/2006 | King | |
| 2006/0259099 A1 | 11/2006 | Goetz et al. | |
| 2006/0293609 A1 | 12/2006 | Stahmann et al. | |
| 2007/0100408 A1 | 5/2007 | Gerber et al. | |
| 2007/0203537 A1 | 8/2007 | Goetz et al. | |
| 2007/0203540 A1 | 8/2007 | Goetz et al. | |
| 2007/0203541 A1 | 8/2007 | Goetz et al. | |
| 2007/0203542 A1 | 8/2007 | Goetz et al. | |
| 2007/0203544 A1 | 8/2007 | Goetz et al. | |
| 2007/0203546 A1 | 8/2007 | Stone et al. | |
| 2008/0004674 A1 | 1/2008 | King et al. | |
| 2008/0046036 A1 | 2/2008 | King et al. | |
| 2008/0071324 A1 | 3/2008 | Miesel et al. | |
| 2008/0082137 A1 | 4/2008 | Kieval et al. | |
| 2008/0109048 A1 | 5/2008 | Moffitt | |
| 2008/0154340 A1 | 6/2008 | Goetz et al. | |
| 2008/0163097 A1 | 7/2008 | Goetz et al. | |
| 2008/0183256 A1 | 7/2008 | Keacher | |
| 2008/0215118 A1 | 9/2008 | Goetz et al. | |
| 2008/0215119 A1 | 9/2008 | Woods et al. | |
| 2008/0221637 A1 | 9/2008 | Woods et al. | |
| 2008/0288023 A1 | 11/2008 | John | |
| 2008/0294211 A1 | 11/2008 | Moffitt | |
| 2009/0018617 A1 | 1/2009 | Skelton et al. | |
| 2009/0024189 A1 | 1/2009 | Lee et al. | |
| 2009/0054946 A1* | 2/2009 | Sommer ............ | A61N 1/36185 607/59 |
| 2009/0149917 A1 | 6/2009 | Whitehurst et al. | |
| 2010/0023069 A1 | 1/2010 | Moffitt et al. | |
| 2010/0023070 A1 | 1/2010 | Moffitt et al. | |
| 2010/0106219 A1 | 4/2010 | Torgerson et al. | |
| 2010/0121409 A1 | 5/2010 | Kothandaraman et al. | |
| 2010/0137926 A1 | 6/2010 | King et al. | |
| 2011/0093044 A1 | 4/2011 | Moffitt | |
| 2011/0307032 A1* | 12/2011 | Goetz ................ | A61N 1/37264 607/59 |
| 2011/0313268 A1 | 12/2011 | Kokones et al. | |
| 2012/0053658 A1* | 3/2012 | Gabriela ............. | A61N 1/0534 607/62 |
| 2013/0131760 A1 | 5/2013 | Rao et al. | |
| 2016/0082261 A1 | 3/2016 | Moffit et al. | |
| 2016/0121124 A1 | 5/2016 | Johanek et al. | |
| 2016/0158564 A1 | 6/2016 | Rao et al. | |
| 2017/0165490 A1 | 6/2017 | Wechter | |
| 2017/0333718 A1 | 11/2017 | Moffitt et al. | |
| 2019/0388695 A1 | 12/2019 | Dinsmoor et al. | |
| 2021/0154480 A1 | 5/2021 | Young-Dixon et al. | |

FOREIGN PATENT DOCUMENTS

| | | | |
|---|---|---|---|
| WO | 2009076211 A1 | 6/2009 | |
| WO | 2009134480 A1 | 11/2009 | |
| WO | 2009137121 A1 | 11/2009 | |
| WO | 2010011721 A1 | 1/2010 | |

OTHER PUBLICATIONS

Bian et al., "Double electrodes simultaneous stimulation and implantation technique in deep brain stimulation," Chin J. Traumatol, vol. 8(4):256-6, Aug. 2005, 1 pp. (English translation of abstract only).

Bourret et al., "Programmable High-Amplitude Balanced Stimulus Current-Source for Implantable Microstimulators," Proceedings of the 19th Annual International Conference of the IEEE Engineering in Medicine and Biology Society, Oct. 30-Nov. 2, 1997, pp. 1938-1941.

Kim et al., "A 64-Site Multishank CMOS Low-Profile Neural Stimulating Probe," IEEE Journal of Solid State Circuits, vol. 31, No. 9, Sep. 1996, pp. 1230-1238.

Lee et al., "AIM Targeting Technique: A Novel Method of Focusing the vol. of Activation on the Dorsal Column with Multiple Independent Current Control in a Computational Model," Boston Scientific Neuromodulation, Valencia, California, presented at 13th North American Neuromodulation Society Annual Meeting, Las Vegas, Nevada, Dec. 3-6, 2009, Poster ID A107, 2 pp.

St-Amand et al., "Design and Optimization of a Low DC Offset CMOS Current-Source Dedicated to Implantable Miniaturized Stimulators," Analog Integrated Circuits and Signal Processing, vol. 11, Applicant points out, in accordance with MPEP 609.04(a), that the year of publication, 1996, is sufficiently earlier than the effective U.S. filing date, so that the particular month of publication is not in issue, pp. 47-61.

(56) References Cited

OTHER PUBLICATIONS

Extended Search Report from counterpart European Application No. 21210495.4 dated Apr. 22, 2022, 7 pp.

* cited by examiner

SEGMENTED LEAD INDEPENDENT ELECTRODE CONTROL FOR SENSING OR ADAPTIVE STIMULATION

This application claims the benefit of U.S. Provisional Application No. 63/118,470, filed Nov. 25, 2020, and entitled "SEGMENTED LEAD INDEPENDENT ELECTRODE CONTROL FOR SENSING OR ADAPTIVE STIMULATION," the entire content of which is incorporated by reference herein.

TECHNICAL FIELD

The disclosure relates to medical devices and, more particularly, to medical devices that deliver electrical stimulation therapy.

BACKGROUND

Medical devices may be used to treat a variety of medical conditions. Medical electrical stimulation devices, for example, may deliver electrical stimulation therapy to a patient via electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. The electrical stimulation device may comprise a leadless stimulator. In some cases, implantable electrodes may be coupled to an external electrical stimulation generator via one or more percutaneous leads or fully implanted leads.

Medical electrical stimulators may be used to deliver electrical stimulation therapy to patients to relieve a variety of symptoms or conditions such as chronic pain, tremor, Parkinson's disease, depression, epilepsy, urinary or fecal incontinence, pelvic pain, sexual dysfunction, obesity, or gastroparesis. An electrical stimulator may be configured to deliver electrical stimulation therapy via leads that include electrodes proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

A clinician may select values for a number of programmable parameters in order to define the electrical stimulation therapy to be delivered by the implantable stimulator to a patient. For example, the clinician may select one or more electrodes for delivery of the stimulation, a polarity of each selected electrode, a voltage or current amplitude, a pulse width, a pulse frequency, and/or a duty cycle as stimulation parameters. A set of parameters, such as a set including electrode combination, electrode polarity, amplitude, pulse width and pulse rate, may be referred to as a program in the sense that they define the electrical stimulation therapy to be delivered to the patient.

Some medical electrical stimulators may be sensing or adaptive medical electrical stimulators. In addition to delivering electrical stimulation therapy to a patient, such sensing or adaptive medical electrical stimulators may sense a response to the delivered stimulation signal via electrodes on one or more leads and adapt the electrical stimulation therapy being delivered to the patient based on the sensed response. For example, such medical electrical stimulators may change one or more stimulation parameters, such as amplitude, pulse width, frequency, duty cycle, which electrodes are used for electrical stimulation, or change a stimulation program based on the sensed response.

SUMMARY

In general, this disclosure describes medical systems that are sensing or adaptive and techniques for delivering sensing or adaptive electrical stimulation and providing Independent Electrode Control (IEC) for use in stimulation therapy. These medical systems and techniques may deliver electrical stimulation that is sensing or adaptive using segmented leads (e.g., leads having groups of segmented electrodes), while avoiding or mitigating the introduction of sense artifacts. While primarily discussed in the context of a sensing or adaptive deep brain stimulation (aDBS) system, the systems and techniques described herein may be used for other stimulation therapies.

In particular, this disclosure describes medical systems configured to deliver and techniques for delivering symmetrical electrical stimulation to a patient and sense a response of the patient to the symmetrical electrical stimulation signal. In some examples, the medical system may also be adaptive and the techniques may adaptively deliver symmetrical electrical stimulation. Delivering of symmetrical electrical stimulation may refer to delivering electrical stimulation that is substantially the same between electrodes or segment electrodes in different groups of segmented electrodes. The medical system may deliver the symmetrical electrical stimulation through a segmented lead. In accordance with various techniques of this disclosure, an electrical stimulation system delivers symmetrical electrical stimulation to the patient via the lead(s), senses a response to the symmetrical electrical stimulation signal, and adapts the electrical stimulation therapy based on the sensed response. By delivering electrical stimulation in a symmetrical manner, the electrical stimulation system may avoid sensing artifacts of the stimulation signal which may otherwise adversely affect the sensing of the response to the electrical stimulation signal.

In one example, this disclosure is directed to a system including a lead comprising a first electrode disposed at a first level, a second electrode disposed at a second level, a first group of segmented electrodes disposed at a third level, and a second group of segmented electrodes disposed at a fourth level; and a medical device configured to deliver symmetrical electrical stimulation to a patient via at least one of the first electrode, the second electrode, at least one segment electrode of the first group of segmented electrodes, or at least one segment electrode of the second group of segmented electrodes and sense a response to the symmetrical electrical stimulation via at least two of the first electrode, the second electrode, at least one other segment electrode of the first group of segmented electrodes, or at least one other segment electrode of the second group of segmented electrodes.

In another example, the disclosure is directed to a neuromodulation system including a stimulation generator configured to deliver symmetrical electrical stimulation through at least one of a first electrode, a second electrode, at least one segment electrode of a first group of segmented electrodes or at least one segment electrode of a second group of segmented electrodes; a sensing channel configured to sense a response to of the symmetrical electrical stimulation through at least two of the first electrode, the second electrode, at least one other segment electrode of the first group of segmented electrodes or at least one other segment electrode of the second group of segmented electrodes, and processing circuitry configured to: control the stimulation generator to deliver the symmetrical electrical stimulation; determine a response to the stimulation via the sensing channel; and adjust at least one stimulation parameter of the symmetrical electrical stimulation based on the sensed response.

In another example, the disclosure is directed to a method including generating a symmetrical electrical stimulation signal, delivering the symmetrical electrical stimulation signal through at least one of a first electrode, a second electrode, at least one segment electrode of a first group of segmented electrodes or at least one segment electrode of a second group of segmented electrodes to a patient, sensing a response to the symmetrical electrical stimulation signal through at least two of the first electrode, the second sensing electrode, at least one other segment electrode of a first group of segmented electrodes or at least one other segment electrode of a second group of segmented electrodes, and adjusting at least one stimulation parameter of the symmetrical electrical stimulation signal based on the sensed response.

In another example, the disclosure is directed to a computer-readable storage storing instructions, which, when executed, cause processing circuitry to control a stimulation generator to generate a symmetrical electrical stimulation signal, control the stimulation generator to deliver the symmetrical electrical stimulation signal through at least one of a first electrode, a second electrode, at least one segment electrode of a first group of segmented electrodes, or at least one segment electrode of a second group of segmented electrodes to a patient, sense a response to the symmetrical electrical stimulation signal through at least two of a first electrode, a second electrode, at least one other segment electrode of the first group of segmented electrodes, or at least one other segment electrode of the second group of segmented electrodes, and control the stimulation generator to adjust at least one stimulation parameter of the symmetrical electrical stimulation signal based on the sensed response.

The details of one or more aspects of the disclosure are set forth in the accompanying drawings and the description below. Other features, objects, and advantages will be apparent from the description and drawings, and from the claims.

DETAILED DESCRIPTION

A patient may suffer from one or more symptoms treatable by electrical stimulation therapy. However, the severity of these symptoms may increase or decrease, for example, depending on various conditions such as the posture of the patient, the current activity of the patient (e.g., whether the patient is sleeping, exercising, working, or the like), the stress level of the patient, drug therapy or other therapy administered to the patient, and many other factors. Thus, a system that delivers electrical stimulation therapy with fixed parameters, in some circumstances, may not deliver therapy that is sufficient to treat the symptoms of the patient over a range of conditions. Furthermore, in other circumstances, a fixed parameter therapy delivery system may deliver a higher magnitude of electrical stimulation than is required to treat the symptoms of the patient, which may cause side effects in the patient and/or cause excessive power consumption by an implantable medical device (IMD). Accordingly, it may be desirable to have an electrical stimulator that may sense a response to the electrical stimulation therapy. In some examples, such a response may be used to automatically adjust at least one parameter of the electrical stimulation based on the sensed response. Such an electrical stimulator may be referred to as an adaptive electrical stimulator. In other examples, the response may be used by a clinician to inform the clinician on stimulation therapy optimization which may include the clinician or patient adjusting at least one parameter of the electrical stimulation. Such an electrical stimulator may be referred to as a sensing electrical stimulator.

This disclosure describes various techniques for medical devices to deliver sensing or adaptive electrical stimulation therapy using a groups of segmented electrodes of a lead and sense a response to the electrical stimulation therapy in a patient using other electrodes of the lead. Based on the response, the medical devices may adapt one or more parameters of the therapy being delivered to the patient. The techniques of this disclosure may include delivering the electrical stimulation therapy in a symmetrical manner. By delivering the electrical stimulation therapy in a symmetrical manner, such as delivering electrical stimulation that is substantially the same between segment electrodes in different groups of segmented electrodes as described in more detail below, the electrodes used to sense the response may avoid or mitigate sensing artifacts of the electrical stimulation signal. The artifacts that would otherwise be sensed may interfere with, deteriorate, or otherwise impede the sensing of the response.

Figure 1:
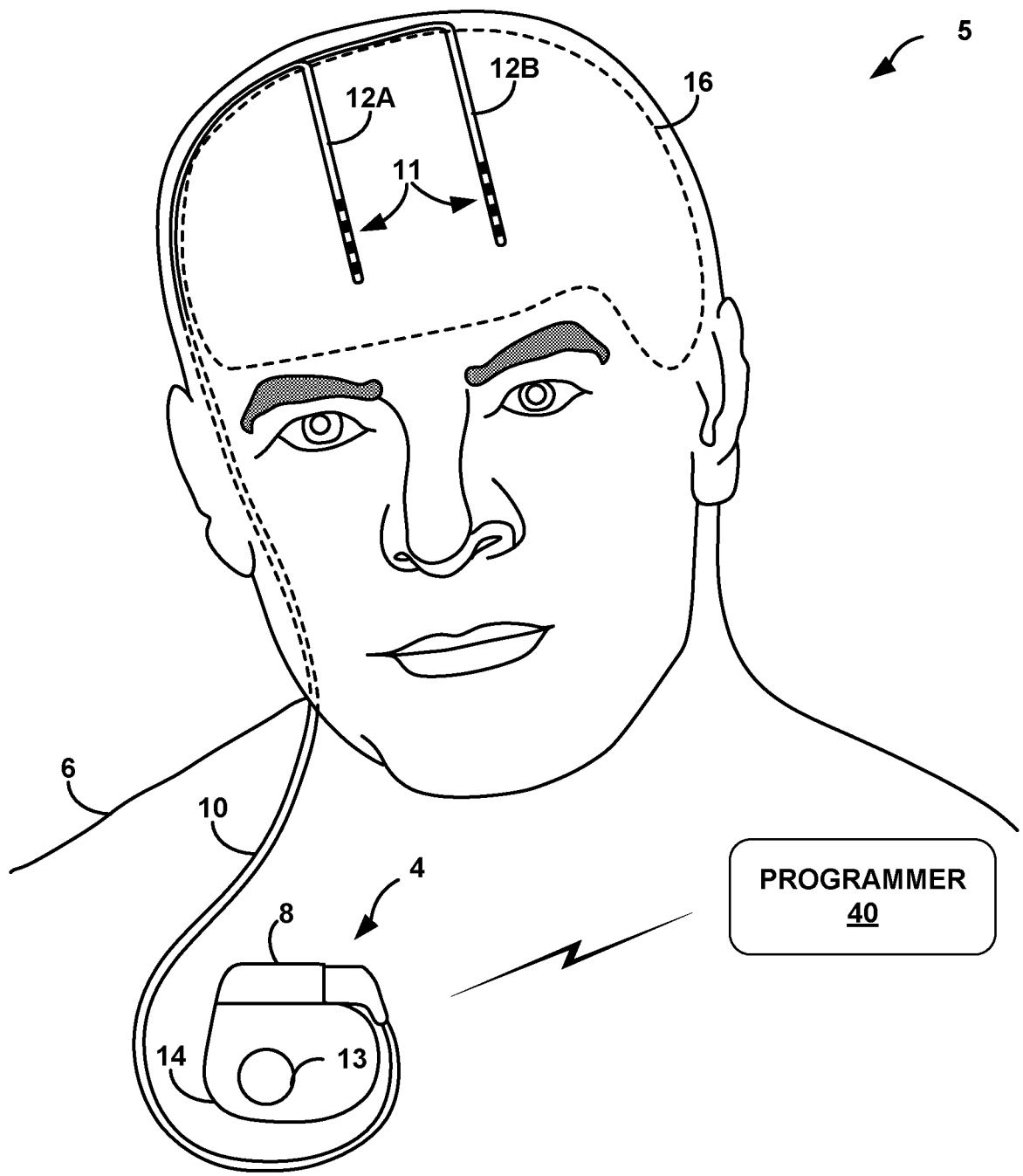
FIG. 1 is a conceptual diagram illustrating an example therapy system that includes an electrical stimulator coupled to a stimulation lead, in accordance with various techniques of this disclosure.

FIG. 1 is a conceptual diagram illustrating an example therapy system 5 that may be used to deliver stimulation therapy to patient 6. In the example of FIG. 1, electrical stimulator 4 may deliver deep brain stimulation (DBS). However, the example techniques are not limited to DBS, and delivery of DBS is provided an example to ease understanding. Patient 6 ordinarily, but not necessarily, will be a human. In some examples, therapy system 5 may be adaptive in the sense that electrical stimulator 4 may adjust, increase, or decrease the magnitude of one or more parameters of the electrical stimulation signal in response to changes in patient activity or movement, a severity of one or more symptoms of a disease of the patient, a presence of one or more side effects due to the DBS, or one or more sensed signals of the patient, etc. For example, one or more sensed signals of patient 6 may be used as a control signal such that electrical stimulator 4 correlates the magnitude of the one or more parameters of the electrical stimulation to the magnitude of the one or more sensed signals.

Generally, therapy system 5 includes electrical stimulator 4 (e.g., an IMD) that delivers electrical stimulation to patient 6 via one or more electrodes. Electrical stimulator 4 may include a master current and a current regulator array allowing electrical stimulator 4 to regulate current sourced or sunk by one or more electrodes 11 on lead portions 12A, 12B of lead 10. As such, electrical stimulator 4 may include a number of current regulator branches that may be used to implement a current regulator for one or more electrodes 11. For purposes of description the electrodes are described as being implantable electrodes. However, the example techniques are not limited to implantable electrodes.

The electrodes 11 may be deployed on one or more medical leads, such as implantable medical lead 10. In some cases, electrical stimulator 4 includes a housing electrode 13 on housing 14. The electrical stimulation may be in the form of controlled current pulses or voltage pulses, or substantially continuous current or voltage waveforms. A stimulation program may define various parameters of the pulses or waveforms. The pulses or waveforms may be delivered substantially continuously or in bursts, segments, or patterns, and may be delivered alone or in combination with pulses or waveforms defined by one or more other stimulation programs.

In some examples, electrical stimulator 4 may deliver, for example, deep brain stimulation (DBS) or cortical stimulation (CS) therapy to patient 6 via the electrodes carried by lead portions 12A and 12B (collectively "lead portions 12"). Although FIG. 1 shows a particular stimulation environment (e.g., DBS), the techniques of this disclosure are not so limited, and electrical stimulator 4 may deliver stimulation therapy to other parts of patient 6, such as the spinal cord of patient 6. For example, other electrical stimulation systems may be configured to deliver electrical stimulation to gastrointestinal organs, pelvic nerves or muscle, peripheral nerves, or other stimulation sites. In addition, although FIG. 1 shows a fully implantable electrical stimulator 4, techniques described in this disclosure may be applied to external stimulators having electrodes deployed via percutaneous leads.

In the example illustrated in FIG. 1, electrical stimulator 4 is implanted in a clavicle region of patient 6. Electrical stimulator 4 generates programmable electrical stimulation (e.g., a current or voltage waveform or current or voltage pulses) and delivers the stimulation through one or more of electrodes 11 via a medical lead 10. Electrical stimulator 4 may also sense a response to the electrical stimulation through one or more electrodes 11 via medical lead 10. An electrode may not simultaneously be used to deliver stimulation and sense a response. In general, delivery of electrical stimulation using controlled current pulses will be described in this disclosure for purposes of illustration. In some cases, electrical stimulator 4 may include multiple leads. In the example of FIG. 1, a distal end of lead 10 is bifurcated and includes lead portions 12. In some examples the distal end of lead 10 is not bifurcated. Lead portions 12A and 12B each include a set of electrodes forming part of the array of electrodes 11. In various examples, lead portions 12A and 12B may each carry a number of electrodes, such as four, eight, or sixteen electrodes. In the example of FIG. 1, each lead portion 12A, 12B carries four electrodes, which may be configured as ring electrodes at different axial positions (or levels) near the distal ends of the lead portions 12 and segmented electrodes at different axial positions. As one example, lead portions 12 may each include two ring electrodes at two different axial positions, and between the two ring electrodes, lead portions 12 may include a plurality of groups of segmented electrodes, where a group of segmented electrodes of the plurality of groups includes two or more electrodes all at approximately the same axial position. Throughout the remainder of this disclosure, for purposes of simplicity, the disclosure may generally refer to electrodes carried on "leads" which may be "lead portions" or the entire lead.

FIG. 1 further depicts a housing electrode 13. Housing electrode 13 may be formed integrally with an outer surface of hermetically-sealed housing 14 of electrical stimulator 4, or otherwise coupled to housing 14. In one example, housing electrode 13 may be described as an active, non-detachable electrode on electrical stimulator 4. In some examples, housing electrode 13 is defined by an uninsulated portion of an outward facing portion of housing 14 of electrical stimulator 4. Other divisions between insulated and uninsulated portions of housing 14 may be employed to define two or more housing electrodes. In some examples, housing electrode 13 comprises substantially all of housing 14, one side of housing 14, a portion of housing 14, or multiple portions of housing 14. In one example implementation of the techniques of this disclosure, e.g., an omnipolar arrangement, one or more electrodes 11 may transfer stimulation pulses from lead 10 to patient 6 substantially simultaneously with stimulation pulses delivered via housing electrode 13.

In some examples, electrical stimulator 4 may be coupled to one or more leads which may or may not be bifurcated. In such examples, the leads may be coupled to electrical stimulator 4 via a common lead extension or via separate lead extensions. A proximal end of lead 10 may be coupled to a header on electrical stimulator 4. Conductors in the lead body may electrically connect stimulation electrodes located on lead portions 12 to electrical stimulator 4. Lead 10 traverses from the implant site of electrical stimulator 4 along the neck of patient 6 to the brain 16 of patient 6. In some examples, lead portions 12A and 12B may be implanted within the right and left hemispheres, respectively, in order to deliver electrical stimulation to one more regions of brain 16.

Lead portions 12A, 12B may be implanted within a desired location of brain 16 through respective holes in the cranium of patient 6. Lead portions 12A, 12B may be placed at any location within brain 16 such that the electrodes located on lead portions 12A, 12B are capable of providing electrical stimulation to targeted tissue. The electrodes of lead portions 12A, 12B are shown as ring electrodes. In some examples, some or all of the electrodes of lead portions 12A, 12B may be groups of segmented electrodes. In some examples, the electrodes of lead portions 12A, 12B may have different configurations. For example, the electrodes of lead portions 12A, 12B may have a complex electrode array geometry that is capable of producing shaped electrical fields. The complex electrode array geometry may include multiple electrodes (e.g., partial ring or segmented electrodes) around the perimeter of each lead portions 12A, 12B. In some examples, lead portions 12 may have shapes other than elongated cylinders as shown in FIG. 1. For example, lead portions 12 may be paddle leads, spherical leads, bendable leads, or any other type of shape effective in treating patient 6. In addition, the electrodes may be electrode pads on a paddle lead, circular electrodes surrounding the body of a lead, conformable electrodes, cuff electrodes, segmented electrodes, or any other type of electrodes capable of forming unipolar, bipolar, multi-polar, etc. electrode configurations.

Therapy system 5 may include a programmer 40, such as an external programmer operated by a clinician or patient. In some examples, a programmer 40 may be a handheld computing device that permits a clinician to program stimulation therapy for patient 6 via a user interface. For example, using programmer 40, the clinician may specify stimulation parameters for use in delivery of stimulation therapy. Programmer 40 may support telemetry with electrical stimulator 4 to download programs and, optionally, upload operational or physiological data stored by electrical stimulator 4. Programmer 40 may also include a display and input keys to allow patient 6 or a clinician to interact with programmer 40 and electrical stimulator 4. In this manner, programmer 40 provides patient 6 with a user interface for control of the stimulation therapy delivered by electrical stimulator 4. For example, patient 6 may use programmer 40 to start, stop or adjust electrical stimulation. In particular, programmer 40 may permit patient 6 to adjust stimulation parameters of a program, such as duration, current or voltage amplitude, pulse width, pulse shape, and pulse rate. Patient 6 may also select a program (e.g., from among a plurality of stored programs) as the present program to control delivery of stimulation by electrical stimulator 4.

In some cases, programmer 40 may be characterized as a physician or clinician programmer 40. For example, programmer 40 may include a clinician programmer if programmer 40 is primarily intended for use by a physician or clinician. In other cases, programmer 40 may be characterized as a patient programmer if programmer 40 is primarily intended for use by a patient. In general, a physician or clinician programmer may support selection and generation of programs by a clinician for use by stimulator 4, whereas a patient programmer may support adjustment and selection of such programs by a patient during ordinary use.

Whether programmer 40 is configured for clinician or patient use, programmer 40 may communicate with electrical stimulator 4 or any other computing device via wireless communication. Programmer 40, for example, may communicate via wireless communication with electrical stimulator 4 using RF telemetry techniques known in the art. Programmer 40 may also communicate with another programmer or computing device via a wired or wireless connection using any of a variety of local wireless communication techniques, such as radio frequency (RF) communication according to the 802.11 or Bluetooth specification sets, infrared communication according to the Infrared Data Association (IrDA) specification set, or other standard or proprietary telemetry protocols. Programmer 40 may also communicate with another programming or computing device via exchange of removable media, such as magnetic or optical disks, or memory cards or sticks. Further, programmer 40 may communicate with electrical stimulator 4 and other programming devices via remote telemetry techniques known in the art, communicating via a local area network (LAN), wide area network (WAN), public switched telephone network (PSTN), or cellular telephone network, for example.

In some examples, electrical stimulator 4 delivers stimulation according to a group of programs at a given time. Each program of such a program group may include respective values for each of a plurality of therapy parameters, such as respective values for each of current or voltage amplitude, pulse width, pulse shape, pulse rate and electrode configuration (e.g., electrode combination and polarity). Electrical stimulator 4 may interleave pulses or other signals according to the different programs of a program group. In such examples, programmer 40 may be used to create programs, and assemble the programs into program groups. In some examples, programmer 40 may be used to adjust stimulation parameters of one or more programs of a program group, and select a program group as the current program group to control delivery of stimulation by electrical stimulator 4.

Generally, therapy system 5 delivers stimulation therapy to patient 6 in the form of constant current or voltage waveforms or constant current or voltage pulses. The shapes of the pulses may vary according to different design objectives, and may include ramped or trapezoidal pulses, sinusoidal or otherwise curved pulses, stepped pulses having two or more discrete amplitudes, closely spaced pairs of pulses, and biphasic (positive and negative aspects within a single pulse) or monophasic (only positive or only negative aspects within a single pulse) variations of any of the above. In the case of current-based stimulation, electrical stimulator 4 regulates current that is sourced or sunk by one or more electrodes 11, referred to as regulated electrodes. In some examples, one or more of the electrodes 11 may be unregulated. In such configurations, the housing electrode 13 and/or a lead electrode 11 may be the unregulated electrode.

A source current may refer to a positive current that flows out of an electrode (anode), whereas a sink current may refer to a negative current that flows into an electrode (cathode). Regulated source currents may sum to produce a greater overall source current (e.g., currents from a plurality of source currents sum together to generate the overall source current). Likewise, regulated sink currents may sum to produce a greater overall sink current (e.g., currents from a plurality of sink currents sum together to generate the overall ink current). Regulated source and regulated sink currents may partially or entirely cancel one another, producing a net difference in the form of a net source current or sink current in the case of partial cancellation. In some examples, an unregulated current path can source or sink current approximately equal to this net difference. In some examples, regulated source and sink currents may be substantially balanced.

As mentioned above, in some example implementations (e.g., omnipolar arrangements), one or more electrodes 11 may transfer stimulation current from lead 10 to the tissue substantially simultaneously with stimulation current delivered to patient 6 from housing electrode 13. In some example implementations (e.g., bipolar/multipolar arrangements), one or more electrodes 11 may be configured to act as anodes and source current while one or more different electrodes 11 may be configured to act as cathodes and sink current. In another example implementation (e.g., unipolar arrangements), housing electrode 13 may be configured to act as an anode and source current while one or more electrodes 11 on one or more leads are configured to act as cathodes and sink current. Techniques of this disclosure may be implemented using unipolar arrangements, bipolar/multipolar arrangements, and omnipolar arrangements.

A user, such as a clinician or patient 6, may interact with a user interface of programmer 40 to program electrical stimulator 4. In accordance with various techniques described in this disclosure, programmer 40 may be used to receive user input, via the user interface indicating a desired electrical current amplitude. Programmer 40 may control electrical stimulator 4 to cause electrical stimulator 4 to deliver stimulation pulses to electrodes at the desired electrical current amplitudes, as described in more detail below, or otherwise program electrical stimulator 4. Programming of electrical stimulator 4 may refer generally to the generation and transfer of commands, programs, or other information to control the operation of electrical stimulator 4. For example, programmer 40 may transmit programs, parameter adjustments, program selections, group selections, or other information to control the operation of electrical stimulator 4. In addition, programming of stimulator 4 may include receiving, via programmer 40, user input indicating a target stimulation zone and controlling the electrical stimulator to transition electrical stimulation from an initial stimulation zone to the target stimulation zone via a sequence of one or more intermediate stimulation zones.

Electrical stimulator 4 and programmer 40 may communicate via cables or a wireless communication, as shown in FIG. 1. Programmer 40 may, for example, communicate via wireless communication with electrical stimulator 4 using RF telemetry techniques. Programmer 40 may also communicate with other programmers using any of a variety of local wireless communication techniques, such as RF communication according to the 802.11 or Bluetooth™ specification sets, infrared communication (e.g., according to the IrDA standard), or other standard or proprietary telemetry protocols. Programmer 40 may include a transceiver to permit bi-directional communication with electrical stimulator 4. In some example, programmer 40 may be configured to create one or more programs for symmetrical electrical stimulation to be executed by electrical stimulator 4.

Figure 2:
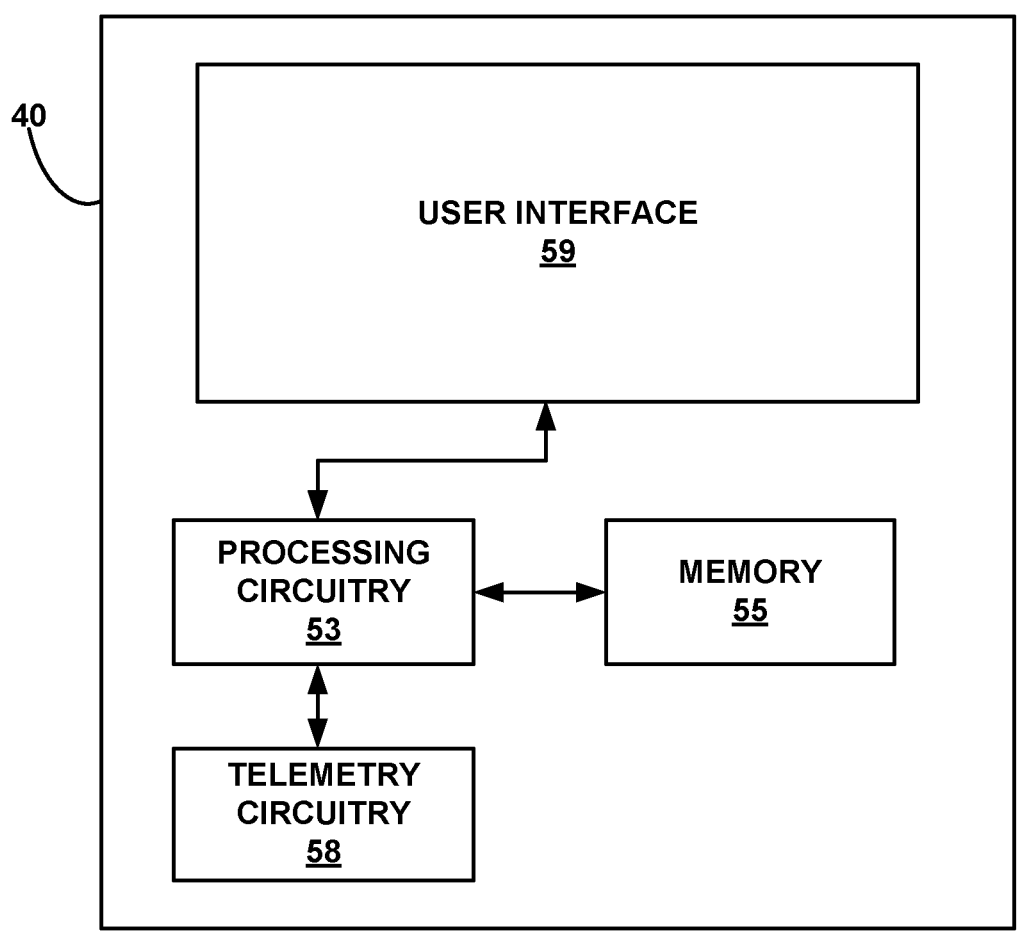
FIG. 2 is a block diagram illustrating various example components of a programmer for use with an electrical stimulator, in accordance with various techniques of this disclosure.

FIG. 2 is a functional block diagram illustrating various components of programmer 40 for an electrical stimulator 4. As shown in FIG. 2, programmer 40 includes processing circuitry 53, memory 55, telemetry circuitry 58, and user interface 59. In general, processing circuitry 53 controls user interface 59, stores and retrieves data to and from memory 55, and controls transmission of data with electrical stimulator 4 through telemetry circuitry 58. Processing circuitry 53 may take the form of one or more microprocessors, controllers, digital signal processors (DSPs), application-specific integrated circuits (ASICs), field-programmable gate arrays (FPGAs), or equivalent discrete or integrated logic circuitry. The functions attributed to processing circuitry 53 herein may be embodied as software, firmware, hardware or any combination thereof.

Memory 55 may store instructions that cause processing circuitry 53 to provide various aspects of the functionality ascribed to programmer 40 herein. Memory 55 may include any fixed or removable magnetic, optical, or electrical media, such as random access memory (RAM), read-only memory (ROM), compact disc ROM (CD-ROM), magnetic memory, electronically-erasable programmable ROM (EEPROM), non-volatile random access memory (NVRAM), flash memory, etc. Memory 55 may also include a removable memory portion that may be used to provide memory updates or increases in memory capacities. A removable memory may also allow patient data to be easily transferred from programmer 40 to another computing device. Memory 55 may also store information that controls operation of electrical stimulator 4.

Telemetry circuitry 58 allows the transfer of data to and from electrical stimulator 4. Telemetry circuitry 58 may communicate automatically with electrical stimulator 4 at a scheduled time or when telemetry circuitry 58 detects the proximity of electrical stimulator 4. Alternatively, telemetry circuitry 58 may communicate with electrical stimulator 4 when signaled by a user through user interface 59. To support RF communication, telemetry circuitry 58 may include appropriate electronic components, such as amplifiers, filters, mixers, encoders, decoders, etc.

In some examples, programmer 40 may communicate wirelessly with electrical stimulator 4 using, for example, RF communication or proximal inductive interaction. This wireless communication is possible through the use of telemetry circuitry 58 which may be coupled to an antenna. Programmer 40 may also be configured to communicate with another computing device via wireless communication techniques, or direct communication through a wired, e.g., network, connection. Examples of local wireless communication techniques that may be employed to facilitate communication between programmer 24 and another computing device include RF communication based on the 802.11 or Bluetooth specification sets, infrared communication.

Programmer 40 may include a user interface 59. A user (e.g., a clinician or patient 6) may interact with user interface 59 in order to, for example, manually select, change or modify programs, adjust voltage or current amplitude of stimulation pulses delivered by specific electrodes or a plurality of electrodes, or view stimulation data. User interface 59 may include a screen and one or more input buttons or input fields that allow programmer 40 to receive input from a user. The screen may be a liquid crystal display (LCD), plasma display, dot matrix display, or touch screen. The input buttons may include a touch pad, increase or decrease buttons/keys, and other input media needed to control electrical stimulation.

Figure 3:
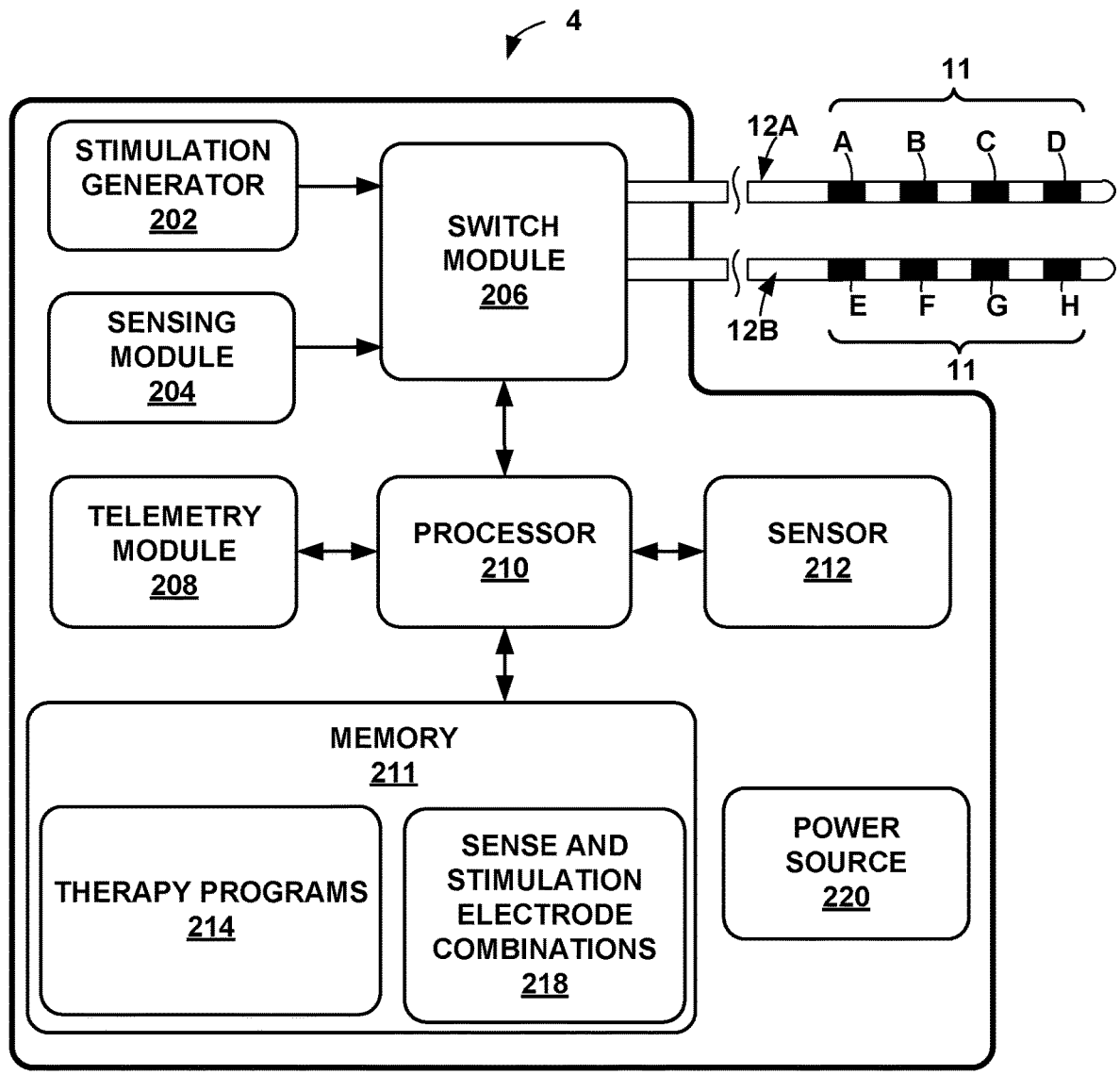
FIG. 3 is a block diagram illustrating various example components of an electrical stimulator in accordance with various techniques of this disclosure.

FIG. 3 is a block diagram of the example electrical stimulator 4 of FIG. 1 for delivering deep brain stimulation therapy and sensing a response thereto. In the example shown in FIG. 3, electrical stimulator 4 includes processor 210, memory 211, stimulation generator 202, sensing module 204, switch module 206, telemetry module 208, sensor 212, and power source 220. Each of these modules may be or include electrical circuitry configured to perform the functions attributed to each respective module. For example, processor 210 may include processing circuitry, switch module 206 may include switch circuitry, sensing module 204 may include sensing circuitry, and telemetry module 208 may include telemetry circuitry. Memory 211 may include any volatile or non-volatile media, such as a random-access memory (RAM), read only memory (ROM), non-volatile RAM (NVRAM), electrically erasable programmable ROM (EEPROM), flash memory, and the like. Memory 211 may store computer-readable instructions that, when executed by processor 210, cause electrical stimulator 4 to perform various functions. Memory 211 may be a storage device or other non-transitory medium.

In the example shown in FIG. 3, memory 211 stores therapy programs 214 and sense electrode combinations and associated stimulation electrode combinations 218 in separate memories within memory 211 or separate areas within memory 211. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Sense and stimulation electrode combinations 218 stores sense electrode combinations and associated stimulation electrode combinations. In some examples, the sense and stimulation electrode combinations may include the same subset of electrodes 11A-11H, a housing of electrical stimulator 4 functioning as an electrode, or may include different subsets or combinations of such electrodes. Thus, memory 211 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processor 210. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In some examples, as discussed above, stimulation may be delivered via a stimulation electrode combination to a tissue site that is different than the tissue site closest to the corresponding sense electrode combination but is within the same region, e.g., the thalamus, of brain 16 in order to mitigate any irregular oscillations or other irregular brain activity within the tissue site associated with the sense electrode combination.

Stimulation generator 202, under the control of processor 210, generates stimulation signals for delivery to patient 6 via selected combinations of electrodes 11A-H. An example range of electrical stimulation parameters believed to be effective in DBS to manage a movement disorder of patient include:

1. Pulse Rate, i.e., Frequency: between approximately 40 Hertz and approximately 500 Hertz, such as between approximately 40 to 185 Hertz or such as approximately 140 Hertz.
2. In the case of a voltage controlled system, Voltage Amplitude: between approximately 0.1 volts and approximately 50 volts, such as between approximately 2 volts and approximately 3 volts.
3. In the alternative case of a current controlled system, Current Amplitude: between approximately 0.2 milliamps to approximately 100 milliamps, such as between approximately 1.3 milliamps and approximately 2.0 milliamps.
4. Pulse Width: between approximately 10 microseconds and approximately 5000 microseconds, such as between approximately 100 microseconds and approximately 1000 microseconds, or between approximately 180 microseconds and approximately 450 microseconds.

Accordingly, in some examples, stimulation generator 202 generates electrical stimulation signals in accordance with the electrical stimulation parameters noted above. Other ranges of therapy parameter values may also be useful, and may depend on the target stimulation site within patient 6. While stimulation pulses are described, stimulation signals may be of any form, such as continuous-time signals (e.g., sine waves) or the like.

Processor 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 210 herein may be embodied as firmware, hardware, software or any combination thereof. Processor 210 may control stimulation generator 202 according to therapy programs 214 stored in memory 211 to apply particular stimulation parameter values specified by one or more of programs, such as voltage amplitude or current amplitude, pulse width, or pulse rate.

In the example shown in FIG. 3, lead portion 12A includes electrodes 11A, 11B, 11C, and 11D, and lead portion 12B includes electrodes 11E, 11F, 11G, and 11H. Processor 210 also controls switch module 206 to apply the stimulation signals generated by stimulation generator 202 to selected combinations of electrodes 11A-11H. In particular, switch module 206 may couple stimulation signals to selected conductors within lead 10 (FIG. 1), which, in turn, deliver the stimulation signals across selected electrodes 11A-11H. Switch module 206 may be a switch array, switch matrix, multiplexer, or any other type of switching module configured to selectively couple stimulation energy to selected electrodes 11A-11H and to selectively sense neurological brain signals with selected electrodes 11A-11H. Hence, stimulation generator 202 is coupled to electrodes 11A-11H via switch module 206 and conductors within lead 10. In some examples, however, electrical stimulator 4 does not include switch module 206.

Stimulation generator 202 may be a single channel or multi-channel stimulation generator. In particular, stimulation generator 202 may be capable of delivering a single stimulation pulse, multiple stimulation pulses, or a continuous signal at a given time via a single electrode combination or multiple stimulation pulses at a given time via multiple electrode combinations. In some examples, however, stimulation generator 202 and switch module 206 may be configured to deliver multiple channels on a time-interleaved basis. For example, switch module 206 may serve to time divide the output of stimulation generator 202 across different electrode combinations at different times to deliver multiple programs or channels of stimulation energy to patient 6. Alternatively, stimulation generator 202 may comprise multiple voltage or current sources and sinks that are coupled to respective electrodes to drive the electrodes as cathodes or anodes. In this example, electrical stimulator 4 may not require the functionality of switch module 206 for time-interleaved multiplexing of stimulation via different electrodes.

Electrodes 11A-11H on respective lead portions 12A, 12B may be constructed of a variety of different designs. For example, one or both of lead portions 12A, 12B may include two or more electrodes at each longitudinal location along the length of the lead portion, such as multiple electrodes at different perimeter locations around the perimeter of the lead at each of the locations A, B, C, and D, and E, F, G, and H. In one example, the electrodes may be electrically coupled to switch module 206 via respective wires that are straight or coiled within the housing the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead portions 12A-12B. These and other constructions may be used to create a lead with a complex electrode geometry.

Although sensing module 204 is incorporated into a common housing with stimulation generator 202 and processor 210 in FIG. 2, in other examples, sensing module 204 may be in a separate housing from electrical stimulator 4 and may communicate with processor 210 via wired or wireless communication techniques. Example neurological brain signals include, but are not limited to, a signal generated from local field potentials (LFPs) within one or more regions of brain 16. EEG and ECoG signals are examples of local field potentials that may be measured within brain 16. However, local field potentials may include a broader genus of electrical signals within brain 16 of patient 6.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. Electrical stimulator 4 may include additional sensors within the housing of electrical stimulator 4 and/or coupled via one of lead portions 12 or other leads. In addition, electrical stimulator 4 may receive sensor signals wirelessly from remote sensors via telemetry module 208, for example. In some examples, one or more of these remote sensors may be external to patient (e.g., carried on the external surface of the skin, attached to clothing, or otherwise positioned external to the patient).

Telemetry module 208 supports wireless communication between electrical stimulator 4 and an external programmer 104 or another computing device under the control of processor 210. Processor 210 of electrical stimulator 4 may receive, as updates to programs, values for various stimulation parameters such as magnitude and electrode combination, from external programmer 40 via telemetry module 208. The updates to the therapy programs may be stored within therapy programs 214 portion of memory 211. Telemetry module 208 in electrical stimulator 4, as well as telemetry modules in other devices and systems described herein, such as external programmer 40, may accomplish communication by radiofrequency (RF) communication techniques. In addition, telemetry module 208 may communicate with external programmer 40 via proximal inductive interaction of electrical stimulator 4 with external programmer 40. Accordingly, telemetry module 208 may send information to external programmer 40 on a continuous basis, at periodic intervals, or upon request from electrical stimulator 4 or external programmer 40.

Power source 220 delivers operating power to various components of electrical stimulator 4. Power source 220 may include a small rechargeable or non-rechargeable battery and a power generation circuit to produce the operating power. Recharging may be accomplished through proximal inductive interaction between an external charger and an inductive charging coil (not shown) within electrical stimulator 4. In some examples, power requirements may be small enough to allow electrical stimulator 4 to utilize patient motion and implement a kinetic energy-scavenging device to trickle charge a rechargeable battery. In other examples, traditional batteries may be used for a limited period of time.

According to the techniques of the disclosure, processor 210 of electrical stimulator 4 delivers, via electrodes 11A-11H interposed along lead portions 12 (and optionally switch module 206), electrical stimulation therapy to patient 6. The DBS therapy is defined by one or more therapy programs 214 having one or more parameters stored within memory 211. For example, the one or more parameters include a current amplitude (for a current-controlled system) or a voltage amplitude (for a voltage-controlled system), a pulse rate or frequency, and a pulse width, or a number of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time.

In one example, processor 210, via some combination of electrodes 11A-H of electrical stimulator 4, monitors the behavior of a signal of patient 6 that correlates to one or more symptoms of a disease of patient 6. In some examples, processor 210, via a different combination of electrodes 11A-11H delivers to patient 6 DBS and may adjust one or more parameters defining the electrical stimulation within a parameter range defined by lower and upper bounds of a therapeutic window based on the activity of the sensed signal.

In one example, the signal is a neurological signal within the Beta frequency band of brain 16 of patient 6. The signal within the Beta frequency band of patient 6 may correlate to one or more symptoms of Parkinson's disease in patient 6. Generally, neurological signals within the Beta frequency band of patient 6 may be approximately proportional to the severity of the symptoms of patient 6. For example, as tremor induced by Parkinson's disease increases, one or more of electrodes 11A-11H detect an increase in the magnitude of neurological signals within the Beta frequency band of patient 6.

Similarly, as tremor induced by Parkinson's disease decreases, processor 210, via the one or more of electrodes 11A-11H, detects a decrease in the magnitude of the neurological signals within the Beta frequency band of patient 6. In another example, the signal is a neurological signal within the Gamma frequency band of brain 16 of patient 6. The signal within the Gamma frequency band of patient 6 may also correlate to one or more side effects of the electrical stimulation therapy. However, in contrast to neurological signals within the Beta frequency band, neurological signals within the Gamma frequency band of patient 6 may be approximately inversely proportional to the severity of the side effects of the electrical stimulation therapy. For example, as side effects due to electrical stimulation therapy increase, processor 210, via the one or more of electrodes 11A-11H, detects a decrease in the magnitude of the signal within the Gamma frequency band of patient 6. Similarly, as side effects due to electrical stimulation therapy decrease, processor 210, via the one or more of electrodes 11A-11H, detects an increase in the magnitude of the signal within the Gamma frequency band of patient 6.

In response to detecting that the signal of the patient, e.g., a sensed physiological parameter signal or a sensed neurological signal, has deviated from the therapeutic window, processor 210 dynamically adjusts the magnitude of the one or more parameters of the electrical stimulation therapy such as, e.g., pulse current amplitude or pulse voltage amplitude, to drive the signal of the patient back into the therapeutic window. For example, wherein the signal is a neurological signal within the Beta frequency band of brain 16 of patient 6, processor 210, via the one or more of electrodes 11A-11H, monitors the beta magnitude of patient 6. Upon detecting that the beta magnitude of patient 6 exceeds the upper bound of the therapeutic window, processor 210 increases a magnitude of the electrical stimulation delivered via electrodes 11A-11H at a maximum ramp rate determined by the clinician until the magnitude of the neurological signal within the Beta band falls back to within the homeostatic window, or until the magnitude of the electrical stimulation reaches an upper limit of a therapeutic window determined by the clinician. Similarly, upon detecting that the beta magnitude of patient 6 falls below the lower bound of the therapeutic window, processor 210 decreases stimulation magnitude at a maximum ramp rate determined by the clinician until the beta magnitude rises back to within the therapeutic window, or until the magnitude of the electrical stimulation reaches a lower limit of the therapeutic window determined by the clinician. Upon detecting that the beta magnitude is presently within the bounds of the therapeutic window, or has returned to within the bounds of the therapeutic window, processor 210 holds the magnitude of the electrical stimulation constant.

As another example, wherein the signal is a neurological signal within the Gamma frequency band of brain 16 of patient 6, processor 210, via the one or more of electrodes 11A-11H, monitors the gamma magnitude of patient 6. Upon detecting that the gamma magnitude of patient 6 falls below the lower bound of the therapeutic window, processor 210 increases a magnitude of the electrical stimulation delivered via electrodes 11A-11H at a maximum ramp rate determined by the clinician until the gamma magnitude rises back to within the therapeutic window, or until the magnitude of the electrical stimulation reaches an upper limit of a therapeutic window determined by the clinician. Similarly, upon detecting that the gamma magnitude of patient 6 rises above the upper bound of the therapeutic window, processor 210 decreases stimulation at a maximum ramp rate determined by the clinician until the gamma magnitude falls back to within the therapeutic window, or until the magnitude of the electrical stimulation reaches a lower limit of a therapeutic window determined by the clinician. Upon detecting that the gamma magnitude is presently within the bounds of the therapeutic window, or has returned to within the bounds of the therapeutic window, processor 210 holds the magnitude of the electrical stimulation constant.

In some examples, processor 210 continuously measures the signal in real time. In other examples, processor 210 periodically samples the signal according to a predetermined frequency or after a predetermined amount of time. In some examples, processor 210 periodically samples the signal at a frequency of approximately 150 Hertz.

Thus, processor 210 may adjust the magnitude of one or more parameters defining the electrical stimulation therapy only when the signal deviates from the therapeutic window to ensure that under normal conditions, the electrical stimulation remains constant, while still retaining the ability to dynamically increase or decrease the electrical stimulation to adapt to the needs of the patient. For example, processor 210 may adjust the magnitude of one or more parameters such that the electrical stimulation is symmetric or remains symmetric as described herein.

Figure 4:
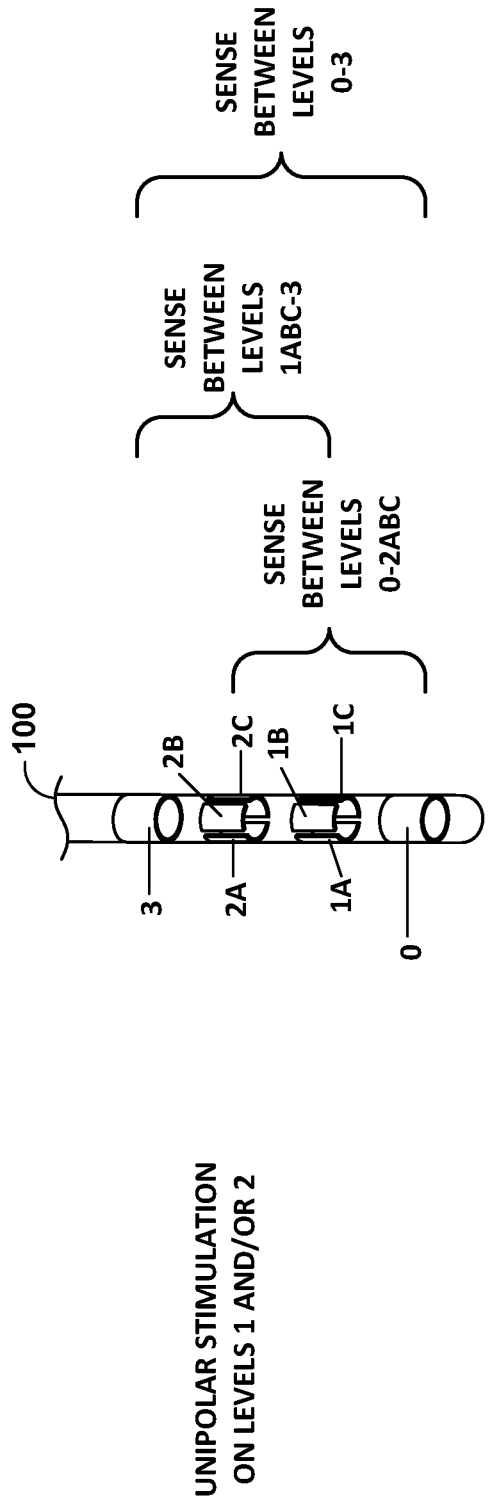
FIG. 4 is a conceptual diagram of an example segmented lead according to the techniques of this disclosure.

FIG. 4 is a conceptual diagram depicting an example segmented lead which may be used by a medical device according to the techniques of this disclosure. In some examples, the segmented lead of FIG. 4 may be a portion of a bifurcated lead, such as lead portion 12A or 12B (FIG. 1). In other examples, the lead of FIG. 4 may not be a bifurcated lead. Segmented lead 100 of FIG. 4 includes a plurality of electrodes. Electrode 0 and electrode 3 are depicted. In the example of FIG. 4, electrode 0 and electrode 3 are depicted as ring electrodes. For example, a ring electrode is an electrode that is shaped like a ring and is disposed all the way around a longitudinal axis of the lead. However, in some examples according to the techniques of this disclosure, one or more of ring electrode 0 or ring electrode 3 may be groups of segmented electrodes. Additionally, group of segmented electrodes 1 and group of segmented electrodes 2 are depicted. Group of segmented electrodes 1 includes segment electrodes 1A, 1B, and 1C. Group of segmented electrodes 2 includes segment electrodes 2A, 2B and 2C. For example, a segment electrode is an electrode that is shaped like a portion or segment of a ring and is disposed partially around the longitudinal axis of the lead. A group of segmented electrodes is a plurality of segment electrodes that are disposed at the same level.

As used herein a location of electrode 0 may be referred to as level 0, a location of group of segmented electrodes 1 may be referred to as level 1, a location of segment electrode 1A may be referred to as level 1A, a location of segment electrode 1B may be referred to as level 1B, a location of segment electrode 1C may be referred to as level 1C, a location of group of segmented electrodes 2 may be referred to as level 2, a location of segment electrode 2A may be referred to as level 2A, a location of segment electrode 2B may be referred to as level 2B, a location of segment electrode 2C may be referred to as level 2C, a location of electrode 3 may be referred to as level 3. While segmented lead 100 is depicted having four levels, any number of levels may be included, according to the techniques of this disclosure. For example, a fifth level may be place between level 1 and level 2. Located at the fifth level may be a ring electrode, a group of segmented electrodes, or another type of electrode. Other implementations including other number and types of electrodes may utilize the techniques of this disclosure. For example, there may be six levels, seven levels, eight levels, etc. Located at each level may be a group of segmented electrodes, a ring electrode, or another type of electrode. A sensing channel may include at least two electrodes that "surround" a stimulation cathode(s). For example, the stimulation cathode(s) may be between the at least two electrodes used for sensing. At a given time, a sensing electrode may not also be a stimulation electrode.

For a group of segmented electrodes, such as group of segmented electrodes 1 or group of segmented electrodes 2, sensing could be configured to use one, two, or all three segment electrodes (segment electrodes 1A-1C or segment electrodes 2A-2C) of the given electrode as part of one electrode set of the sense channel. For 1×4 leads (where the lead has four electrodes and they are all ring electrodes), only the center most electrodes may be used for stimulation. In some implementations, such as a 1×3×3×1 lead (where there is a ring electrode as the distal most electrode, another ring electrode as the proximal most electrode and two three-segment electrodes between the ring electrodes), there may be different configurations available, through which electrical stimulator 4 (of FIG. 1) may deliver stimulation.

Group of segmented electrodes 1 and group of segmented electrodes 2 may be used for stimulation in a unipolar or bipolar configuration. Similarly, in some examples, when using sensing from ring electrode 0 and ring electrode 3, stimulation may be configured on at least one segment electrode of group of segmented electrodes 1 and the same number of segment electrodes of group or segmented electrodes 2 at the same amplitude which may prevent or mitigate stimulation artifacts, such as residual leftover charge. For example, processor 210 (FIG. 3) may sense a same artifact of the electrical stimulation signal on ring electrode 0 and ring electrode 3 due to the stimulation being configured on at least one segment electrode of group of segmented electrodes 1 and the same number of segment electrodes of group or segmented electrodes 2 at the same amplitude and subtract out the artifacts.

When segmented lead 100 is used in a sensing or adaptive electrical stimulation system, electrical stimulator 4 (of FIG. 1) may deliver electrical stimulation to patient 6, such as unipolar electrical stimulation, through any of segment electrodes 1A-1C of group of segmented electrode 1 and/or any of segment electrodes 2A-2C of group of segmented electrodes 2. When electrical stimulator 4 delivers electrical stimulation through both group of segmented electrodes 1 (e.g., through any of segment electrodes 1A-1C or any combination thereof) and group of segmented electrodes 2 (e.g., through any of segment electrodes 2A-2C or any combination thereof), electrical stimulator 4 may sense a response to the electrical stimulation signal through electrode 0 and electrode 3. When electrical stimulator 4 delivers electrical stimulation through group of segmented electrodes 1 (e.g., through any of segment electrodes 1A-1C or any combination thereof), electrical stimulator 4 may sense a response to the electrical stimulation signal through electrode 0 and group of segmented electrodes 2. When electrical stimulator 4 delivers electrical stimulation through group of segmented electrodes 2 (e.g., through any of segment electrodes 2A-2C or any combination thereof), electrical stimulator 4 may sense a response to the electrical stimulation signal through group of segmented electrodes 1 and electrode 3.

Table 1 below shows which electrodes (or segments thereof) may be utilized for stimulation in an adaptive or sensing stimulation system for each sense channel pair in some examples.

TABLE 1

| Sense Channel Pair | Group of Segmented Electrodes 1 (1 × 3 × 3 × 1) | Group of Segmented Electrodes 2 (1 × 3 × 3 × 1) | Electrode 1 (1 × 4 lead) | Electrode 2 (1 × 4 lead) |
|---|---|---|---|---|
| 0-2 | One or more of 1A, 1B, 1C | None | 1 | None |
| 1-3 | None | One or more of 2A, 2B, 2C | None | 2 |
| 0-3 | At least one of 1A, 1B, 1C | Same number of electrodes at the same amplitude as level 1. | 1 | 2 |

In deep brain stimulation, a stimulation signal may be several orders of magnitude higher than brain electrical activity. In some cases, the stimulation signal may be on the order of one million times the amplitude of brain electrical activity. Therefore, it may be desirable to attempt to sense the same artifacts of the stimulation signal at both sensing electrodes. As such, electrical stimulator 4 (of FIG. 1) may be configured to subtract the sensed artifacts out of the sensed signal to determine the response to the electrical stimulation. Therefore, it may be desirable to deliver electrical stimulation in a symmetrical manner.

Techniques for IEC are described in U.S. patent application Ser. No. 16/694,549, filed on Nov. 25, 2019, and entitled "INDEPENDENT CONTROL OF ELECTRICAL STIMULATION AMPLITUDE FOR ELECTRODES FOR DELIVERY OF ELECTRICAL STIMULATION THERAPY," which is hereby incorporated by reference in its entirety. Electrical stimulator 4 may use the techniques of U.S. patent application Ser. No. 16/694,549 to independently control stimulation amplitude for any number of electrodes, such as electrodes 11A-11H (FIG. 3). For example, according to the techniques of this disclosure, electrical stimulator 4 may independently control stimulation amplitude to provide stimulation in a symmetrical manner.

Symmetrical stimulation is now discussed. For IEC enabled systems, stimulation may be balanced longitudinally (or symmetrically) while using sensing or adaptive stimulation. This can be achieved in a number of ways.

In one example, group of segmented electrodes 1 and group of segmented electrodes 2 may form an electrode pair. As such, according to this example, electrical stimulator 4 may deliver the same amplitude stimulation signal through segment electrode 1A as through segment electrode 2A, through segment electrode 1B as through segment electrode 2B, and through segment electrode 1C as through segment electrode 2C. For example, if electrical stimulator 4 is delivering stimulation at 0.5 mA through segment electrode 1A, delivering stimulation at 0.2 mA at segment electrode 1B, and delivering no stimulation through segment electrode 1C, then electrical stimulator 4 may also be delivering stimulation at 0.5 mA through segment electrode 2A, delivering stimulation at stimulation at 0.2 mA through segment electrode 2B, and delivering no stimulation through segment electrode 2C. In other words, in this example, segment electrode 1A amplitude=segment electrode 2A amplitude, segment electrode 1B amplitude=segment electrode 2B amplitude, and segment electrode 1C amplitude=segment electrode 2C amplitude. In this manner, the stimulation being delivered may be symmetrical.

In other examples, the stimulation may be said to be symmetrical if, for each segment electrode of a group of segment electrodes that is paired with another group of segment electrodes, through which electrical stimulator 4 is delivering stimulation, there is a corresponding segment electrode in the other group of segment electrodes of the pair that is delivering stimulation at a same amplitude. In other words, for each segment electrode of one group of segmented electrodes stimulating at a given amplitude, there is a segment electrode of the other group of segmented electrodes that is stimulating at the same given amplitude. For example, if electrical stimulator 4 is delivering stimulation at 0.5 mA through segment electrode 1A, delivering stimulation at 0.2 mA through segment electrode 1B, and not delivering stimulation through segment electrode 1C, then electrical stimulator 4 is delivering through any one of segment electrodes 2A-2C stimulation at 0.5 mA, delivering stimulation at 0.2 mA through another of segment electrodes 2A-2C, and not delivering stimulation through the remaining segment electrode of segment electrodes 2A-2C.

In a further example, the stimulation may be said to be symmetrical if the total amplitude of stimulation being delivered by the segment electrodes of group of segmented electrodes 1 equals the total amplitude of stimulation being delivered by the segment electrodes of group of segmented electrodes 2. For example, if electrical stimulator 4 is delivering stimulation at 0.5 mA through segment electrode 1A, delivering stimulation at 0.2 mA through segment electrode 1B, and not delivering stimulation through segment electrode 1C (a total amplitude of 0.5 mA+0.2 mA+0 mA=0.7 mA), then electrical stimulator 4 may deliver stimulation of a total amplitude of 0.7 mA through each of the segment electrodes 2A-2C. For example, electrical stimulator 4 may deliver stimulation of 0.1 mA amplitude on segment electrode 2A, deliver stimulation of 0.5 mA on segment electrode 2B, and deliver stimulation of 0.1 mA on segment electrode 2C (a total amplitude of 0.1 mA+0.5 mA+0.1 mA=0.7 mA). In this example, stimulation is symmetrical if the amplitude of stimulation through segment electrode 2A+amplitude of stimulation through segment electrode 2B+amplitude of stimulation through segment electrode 2C is equal to amplitude of stimulation through segment electrode 1A+amplitude of stimulation through segment electrode 1B+amplitude of stimulation through segment electrode 1C.

By delivering symmetrical electrical stimulation, electrical stimulator 4 may sense a same artifact in both sensing electrodes along with the response to the symmetrical electrical stimulation and may subtract out the artifact from the sensed response. In this manner, the symmetrical electrical stimulation may reduce the impact of stimulation artifacts.

In some examples, segmented lead 100 may be configured to turn amplitudes around the longitudinal axis of the lead to different segment electrodes of the groups of segmented electrodes like a lighthouse. In other words, a first group of segmented electrodes (e.g., group of segmented electrodes 1) and a second group of segmented electrodes (e.g., group of segmented electrodes 2) may be configured to deliver symmetrical stimulation (according to any of the definitions herein) via different segment electrodes over time.

Figure 5:
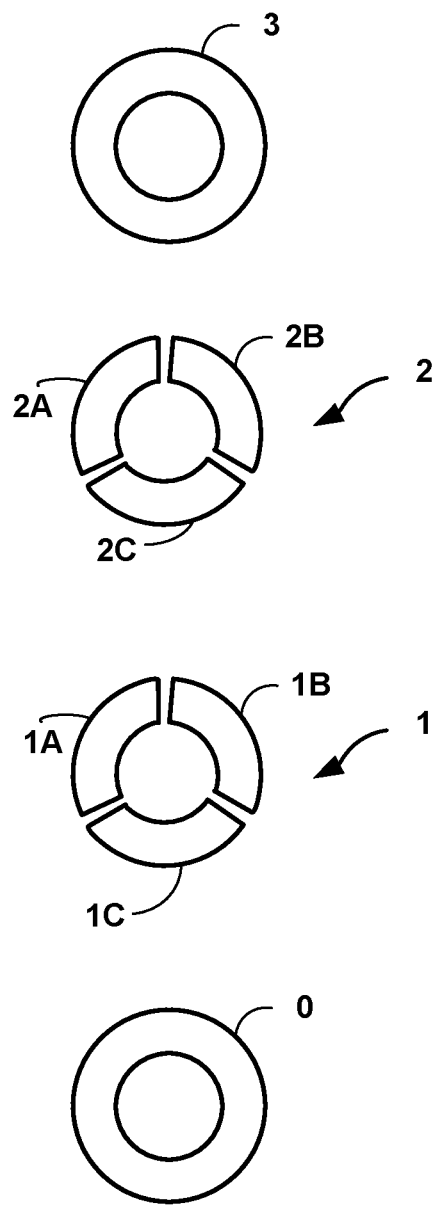
FIG. 5 is a conceptual diagram illustrating an example planar view of each of the electrodes of FIG. 4 according to the techniques of this disclosure.

FIG. 5 is a conceptual diagram illustrating an example planar view of each of the electrodes of FIG. 5 according to the techniques of this disclosure. Electrode 0 is depicted as a ring electrode, as is electrode 3. Group of segmented electrodes 1 is depicted as including segment electrodes 1A-1C. Group of segmented electrodes 2 is depicted as including segment electrodes 2A-2C. While group of segmented electrodes 1 and group of segmented electrodes 2 are each depicted as each including three segment electrodes, group of segmented electrodes 1 and group of segmented electrodes 2 may have another number of segments, such as two, four, five, etc. according to the techniques of this disclosure. If electrical stimulator 4 (of FIG. 1) delivers stimulation through only one of group of segmented electrodes 1 or group of segmented electrodes 2, the electrical stimulation may be said to be symmetrical with respect to the sensing electrodes being used to sense the response to the electrical stimulation signal. For example, if electrical stimulator 4 delivers an electrical stimulation signal through segment electrode 1A, segment electrode 1B, segment electrode 1C, or any combination thereof, the electrical stimulation may be said to be symmetrical with respect to electrode 0 and group of segmented electrodes 2 that are performing the sensing as described above.

However, if electrical stimulator 4 is delivering electrical stimulation through both group of segmented electrodes 1 and group of segmented electrodes 2, the electrical stimulation may or may not be symmetrical with respect to electrode 0 and electrode 3 performing the sensing. If electrical stimulator is delivering stimulation through only one of group of segmented electrodes 1 or group or segmented electrodes 2, the electrical stimulation may not be symmetrical with respect to electrode 0 and electrode 3.

Figure 6:
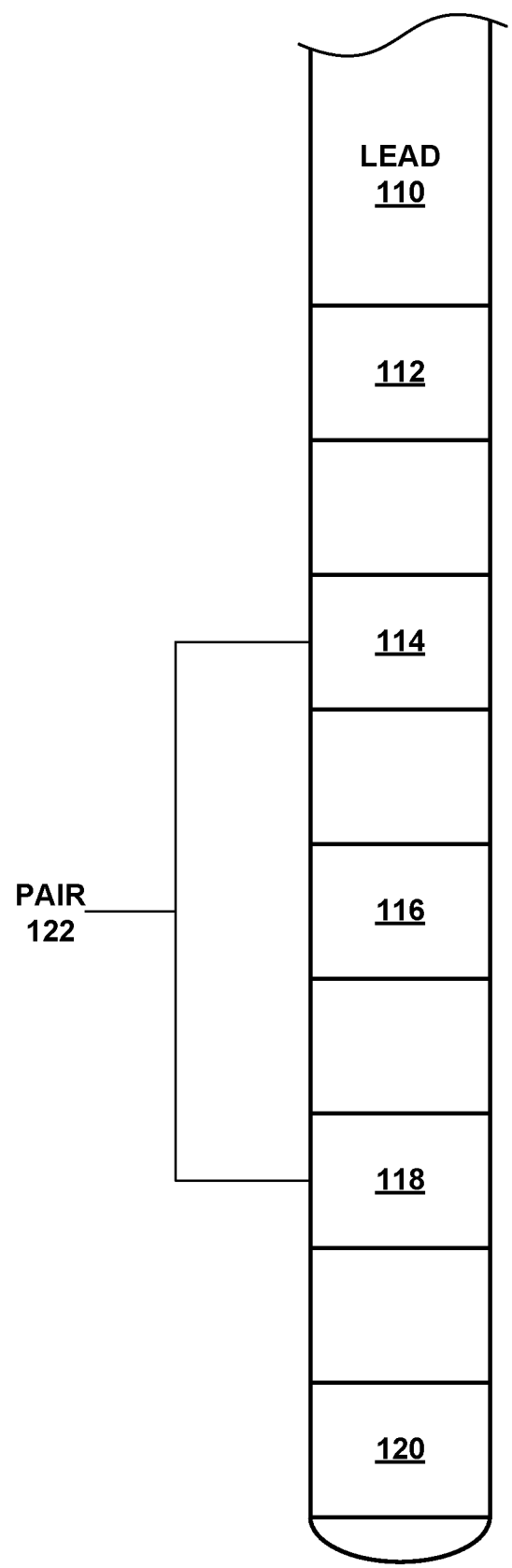
FIG. 6 is a conceptual diagram of an example lead having paired electrodes according to the techniques of this disclosure.

FIG. 6 is a conceptual diagram of an example lead having paired electrodes according to the techniques of this disclosure. In some examples, the lead of FIG. 6 may be a portion of a bifurcated lead, such as lead portion 12A or 12B (FIG. 1). In other examples, the lead of FIG. 6 may not be a bifurcated lead. In this example, there is an odd number of electrodes (or groups of segmented electrodes) being used for stimulation. Lead 110 is depicted having sensing electrode 112 and sensing electrode 120. In some examples, sensing electrode 112 and/or sensing electrode 120 may be ring electrodes. In other examples, sensing electrode 112 and/or sensing electrode 120 may be segmented electrodes. Electrode 114, electrode 116 and electrode 118 are also depicted. In this example, electrodes 114, 116 and 118 are used for stimulation. In some examples, electrode 114, electrode 116, and/or electrode 118 are groups of segmented electrodes. In some examples, electrode 114, electrode 116, and/or electrode 118 are ring electrodes.

The use of symmetrical stimulation is now discussed with reference to FIG. 6. For example, in deep brain stimulation, a stimulation signal may be several orders of magnitude higher than brain electrical activity. In some cases, the stimulation signal may be on the order of one million times the amplitude of brain electrical activity. Therefore, it may be important to attempt to sense the same artifacts of the stimulation signal at each of sensing electrode 112 and sensing electrode 120. As such, electrical stimulator 4 (of FIG. 1) may subtract the sensed artifacts out of the sensed signal to determine the response to the electrical stimulation. In order to enable the sensing of the same artifacts of the stimulation signal at sensing electrode 112 and sensing electrode 120, electrical stimulator 4 may deliver stimulation through electrodes 114, 116 and 118 in a symmetrical manner.

In some examples, electrical stimulator 4 (of FIG. 1) may deliver symmetrical stimulation through lead 110 as follows. Electrode 114 and electrode 118 may form electrode pair 122 as they are the closest electrodes to sensing electrode 112 and sensing electrode 120, respectively. As there are three stimulation electrodes in this example, electrode 116 is not paired with another electrode. Electrical stimulator 4 may deliver any stimulation through electrode 116. However, in some examples where electrode 114 and electrode 118 are groups of segmented electrodes, to deliver symmetrical stimulation, electrical stimulator 4 may deliver electrical stimulation that is of the same amplitude at each respective segment electrode of electrode pair 122.

In some examples, there may be additional pairs of electrodes. These paired electrodes may be located relatively the same distance or in the same order from sensing electrodes 112 and 120. In examples where there are more than four electrodes, if there are an odd number of electrodes being used for stimulation, the innermost or center electrode with respect to the sensing electrodes may be used to provide stimulation of any amplitude. Further electrodes delivering stimulation may be paired based on their proximity to the center electrode (or the sensing electrodes). For example, the two electrodes adjacent to the center electrode may be paired. Each pair of electrodes may be used to deliver stimulation in a symmetrical manner as defined above. However, each pair need not be used to deliver stimulation in a symmetrical manner with respect to any other pair. For example, electrodes of a pair adjacent to the center electrode may each deliver a total of 7 mA of electrical stimulation while a electrodes of a pair adjacent to the sensing electrodes may each deliver a total stimulation different than 7 mA (e.g., each may deliver 5 mA or each may deliver 10 mA).

Figure 7:
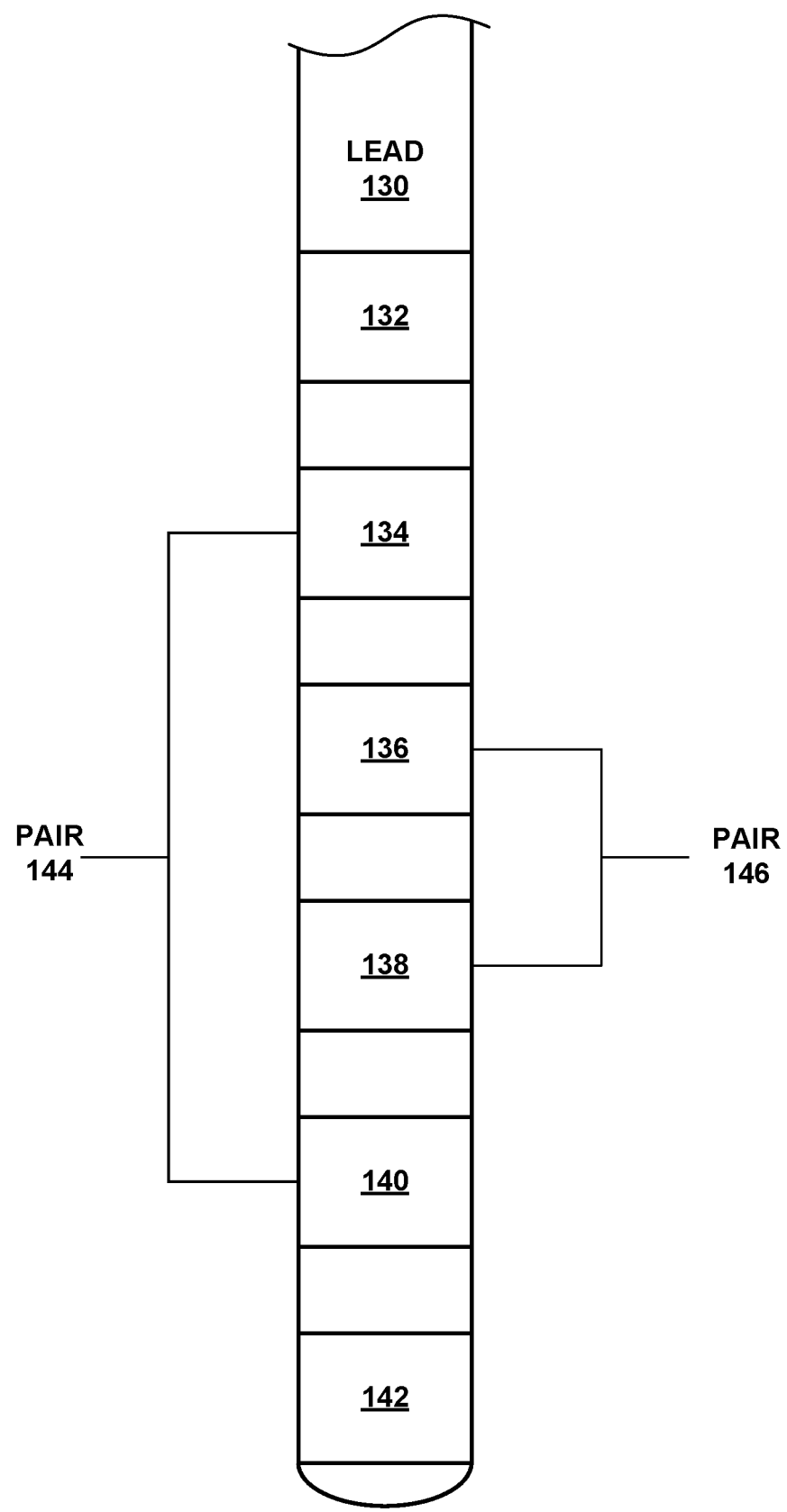
FIG. 7 is a conceptual diagram of another example lead having paired electrodes according to the techniques of this disclosure.

FIG. 7 is a conceptual diagram of another example lead having paired electrodes according to the techniques of this disclosure. In some examples, the lead of FIG. 7 may be a portion of a bifurcated lead, such as lead portion 12A or 12B (FIG. 1). In other examples, the lead of FIG. 7 may not be a bifurcated lead. In this example, lead 130 includes sensing electrode 132 and sensing electrode 142. In some examples, sensing electrode 132 and/or sensing electrode 142 may be ring electrodes. In other examples, sensing electrode 132 and/or sensing electrode 142 may be groups of segmented electrodes. Electrodes 134, 136, 138, and 140 are also depicted. In this example, electrodes 134, 136, 138, and 140 are used for stimulation. In some examples, electrode 134, electrode 136, electrode 138, and/or electrode 140 are groups of segmented electrodes. In some examples, electrode 134, electrode 136, electrode 138, and/or electrode 140 are ring electrodes.

In the example of FIG. 7, there are an even number of electrodes being used for stimulation. In examples, where there are more than four electrodes and there is an even number of electrodes being used for stimulation, each of the electrodes used for stimulation may be paired with another electrode based on the proximity to the sensing electrodes. For example, the electrode closest to one sensing electrode and the electrode closest to another sensing electrode may be paired. For example, electrode 134 is closest to sensing electrode 132, while electrode 140 is closest to sensing electrode 142 and therefore, electrode 134 is paired with electrode 140 to form pair 144. The next closest electrode the first sensing electrode and the next closest electrode to the second sensing electrode may be paired as well. For example, electrode 136 may be paired with electrode 138. This pairing may continue if there are additional electrodes. Electrical stimulator 4 may deliver symmetrical stimulation through each electrode of pair 144 with respect to the other electrode of pair 144 as defined above. Electrical stimulator 4 may also deliver symmetrical stimulation through each electrode of pair 146 with respect to the other electrode of pair 146. The stimulation delivered through pair 144 does not need to be, but may be, symmetrical with respect to pair 146.

Figure 8:
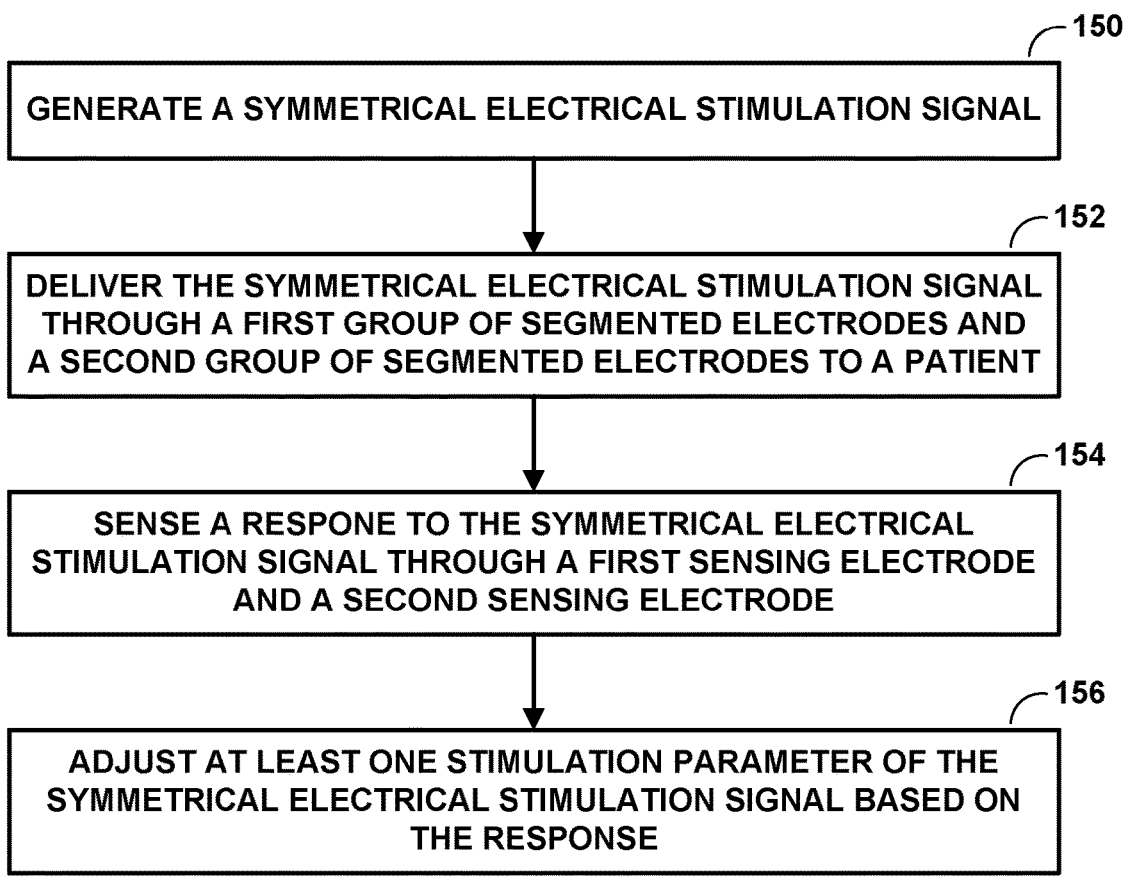
FIG. 8 is a flowchart illustrating symmetrical stimulation techniques of this disclosure.

FIG. 8 is a flowchart illustrating symmetrical stimulation techniques of this disclosure. A device 4 may generate a symmetrical electrical stimulation signal (150). For example, electrical stimulator 4 may generate a symmetrical electrical stimulation signal having a number of parameters, such as frequency, amplitude, pulse width, duty cycle, etc. The device may deliver the symmetrical electrical stimulation signal through a first group of segmented electrodes and a second group of segmented electrodes to a patient (152). For example, electrical stimulator 4 may be electrically coupled to segmented lead 100 (of FIGS. 4 and 5) and may deliver the symmetrical electrical stimulation signal through group of segmented electrodes 1 and group of segmented electrodes 2. It should be noted, that this symmetrical electrical stimulation signal may be delivered through any of segment electrodes 1A-1C or any combination thereof and any of segment electrodes 2A-2C or any combination thereof.

A device may sense a response to the symmetrical electrical stimulation signal through a first sensing electrode and a second sensing electrode (154). For example, electrical stimulator 4 may sense a response to the symmetrical electrical stimulation signal through electrode 0 and electrode 3. For examples, electrode 0 and electrode 3 may for a sense channel and provide electrical stimulator 4 the sensed response. The device may adjust at least one stimulation parameter of the symmetrical electrical stimulation signal based on the sensed response (156). For example, electrical stimulator 4 may adjust the frequency, amplitude, pulse width, duty cycle, and/or which electrodes are used for stimulation based on the sensed response.

In some examples, the symmetrical electrical stimulation signal includes electrical stimulation of a first amplitude through a first segment electrode of the first group of segmented electrodes and a corresponding first segment electrode of the second group of segmented electrodes, stimulation of a second amplitude through a second segment electrode of the first group of segmented electrodes and a corresponding second segment electrode of the second group of segmented electrodes, and stimulation of a third amplitude through a third segment electrode of the first group of segmented electrodes and a corresponding third segment electrode of the second group of segmented electrodes. In some examples, at least one of the first amplitude, the second amplitude, or the third amplitude is 0. In some examples, the first group of segmented electrodes and the second group of segmented electrodes are configured to deliver electrical stimulation via one of current or voltage.

In some examples, the symmetrical electrical stimulation includes for each electrical stimulation amplitude of each segment electrode of the first group of segmented electrodes, a matching electrical stimulation amplitude for one segment electrode of the second group of segmented electrodes. In some examples, the symmetrical electrical stimulation includes a total amplitude of electrical stimulation for each segment electrode of the first group of segmented electrodes equaling a total amplitude of electrical stimulation for each segment electrode of the second group of segmented electrodes.

In some examples, the first group of segmented electrodes and the second group of segmented electrodes are configured to deliver the symmetrical stimulation over different segment electrodes over time. For example, group of segmented electrodes 1 and group of segmented electrodes 2 may be configured to deliver the symmetrical stimulation over different segment electrodes over time, such that the stimulation moves around a longitudinal axis of segmented lead 100 like a light moves around in a lighthouse.

In some examples, a lead may include a third group of segmented electrodes. For example, lead 110 may include electrode 116 (FIG. 6) which may be a third group of segmented electrodes. In some examples, the electrical stimulation delivered by the third group of segmented electrodes may not be symmetrical with the symmetrical electrical stimulation delivered by the first group of segmented electrodes and second group of segmented electrodes. For example, electrode 116 may deliver different stimulation than that delivered by electrodes 114 and 118 (FIG. 6).

In some examples, a lead may further include a fourth group of segmented electrodes. For example, lead 130 (FIG. 7) may include electrodes 134, 136, 138, and 140 which may each be a group of segmented electrodes. The third group of segmented electrodes and the fourth group of segmented electrodes may be configured to deliver symmetrical electrical stimulation to the patient. For example, electrodes 136 and 138 may be configured to deliver symmetrical electrical stimulation to the patient. Likewise, electrodes 134 and 140 may be configured to deliver symmetrical electrical stimulation to the patient. In some examples, the symmetrical stimulation of the first group of segmented electrodes and the second group of segmented electrodes may be different than the symmetrical stimulation of the third group of segmented electrodes and the fourth group of segmented electrodes. For example, the symmetrical stimulation delivered by pair 146 may be different than the symmetrical stimulation delivered by pair 144.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The terms "processor," "processing circuitry," or "controller" or may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, ROM, NVRAM, EEPROM, flash memory, magnetic memory, optical media, or the like. The instructions may be executed to support one or more aspects of the functionality described in this disclosure.

This disclosure includes the following non-limiting examples.

Example 1. A system comprising: a lead comprising: a first electrode disposed at a first level; a second electrode disposed at a second level; a first group of segmented electrodes disposed at a third level; and a second group of segmented electrodes disposed at a fourth level; and a medical device configured to deliver symmetrical electrical stimulation to a patient via at least one of the first electrode, the second electrode, at least one segment electrode of the first group of segmented electrodes, or at least one segment electrode of the second group of segmented electrodes and sense a response to the symmetrical electrical stimulation via at least two of the first electrode, the second electrode, at least one other segment electrode of the first group of segmented electrodes, or at least one other segment electrode of the second group of segmented electrodes.

Example 2. The system of example 1, wherein the medical device is configured to deliver the symmetrical electrical stimulation via at least one segment electrode of the second group of segmented electrodes and sense the response to the symmetrical electrical stimulation via the first electrode and the first group of segmented electrodes.

Example 3. The system of example 1, wherein the medical device is configured to deliver the symmetrical electrical stimulation via at least one segment electrode of the first group of segmented electrodes and at least one segment electrode of the second group of segmented electrodes and sense the response to the symmetrical electrical stimulation via at least one other segment electrode of the first group of segmented electrodes and at least one other segment electrode the second group of segmented electrodes.

Example 4. The system of example 1, wherein the medical device is configured to deliver the symmetrical electrical stimulation via at least two of a first segment electrode of the first group of segmented electrodes, a first segment electrode of the second group of segment electrodes, the first electrode or the second electrode and sense the response to the symmetrical electrical stimulation via a second segment electrode of the first group of segmented electrodes and a second segment electrode of the second group of segmented electrodes.

Example 5. The system of example 1, wherein symmetrical electrical stimulation comprises electrical stimulation of a first amplitude through a first segment electrode of the first group of segmented electrodes and a corresponding first segment electrode of the second group of segmented electrodes, electrical stimulation of a second amplitude through a second segment electrode of the first group of segmented electrodes and a corresponding second segment electrode of the second group of segmented electrodes, and electrical stimulation of a third amplitude through a third segment electrode of the first group of segmented electrodes and a corresponding third segment electrode of the second group of segmented electrodes.

Example 6. The system of example 5, wherein at least one of the first amplitude, the second amplitude, or the third amplitude is 0.

Example 7. The system of any combination of examples 1-6, wherein the medical device is configured to deliver the symmetrical electrical stimulation via one of current or voltage.

Example 8. The system of example 1 or example 7, wherein symmetrical electrical stimulation comprises for each electrical stimulation amplitude of each segment electrode of the first group of segmented electrodes, a matching electrical stimulation amplitude for one segment electrode of the second group of segmented electrodes.

Example 9. The system of example 1 or example 7, wherein symmetrical electrical stimulation comprises a total amplitude of electrical stimulation for each segment electrode of the first group of segmented electrodes equaling a total amplitude of electrical stimulation for each segment electrode of the second group of segmented electrodes.

Example 10. The system of any of examples 1, or 5-9, wherein the first group of segmented electrodes and the second group of segmented electrodes are configured to deliver the symmetrical stimulation via different segment electrodes over time.

Example 11. The system of any of examples 1, or 5-10, further comprising a third group of segmented electrodes, the third group of segmented electrodes being configured to deliver electrical stimulation to the patient.

Example 12. The system of example 11, wherein the electrical stimulation delivered by the third group of segmented electrodes is not symmetrical with the symmetrical electrical stimulation delivered by the first group of segmented electrodes and second group of segmented electrodes.

Example 13. The system of example 11, further comprising a fourth group of segmented electrodes, wherein the third group of segmented electrodes and the fourth group of segmented electrodes are configured to deliver symmetrical electrical stimulation to the patient.

Example 14. The system of example 11, wherein the symmetrical stimulation of the first group of segmented electrodes and the second group of segmented electrodes is different than the symmetrical stimulation of the third group of segmented electrodes and the fourth group of segmented electrodes.

Example 15. An neuromodulation system comprising: a stimulation generator configured to deliver symmetrical electrical stimulation through at least one of a first electrode, a second electrode, at least one segment electrode of a first group of segmented electrodes or at least one segment electrode of a second group of segmented electrodes; a sensing channel configured to sense a response to of the symmetrical electrical stimulation through at least two of the first electrode, the second electrode, at least one other segment electrode of the first group of segmented electrodes or at least one other segment electrode of the second group of segmented electrodes; and processing circuitry configured to: control the stimulation generator to deliver the symmetrical electrical stimulation; determine a response to the stimulation via the sensing channel; and adjust at least one stimulation parameter of the symmetrical electrical stimulation based on the sensed response.

Example 16. The neuromodulation system of example 15, wherein the stimulation generator is configured to deliver the symmetrical electrical stimulation via at least one segment electrode of the second group of segmented electrodes and sense the response to the symmetrical electrical stimulation via the first electrode and the first group of segmented electrodes.

Example 17. The neuromodulation system of example 15, wherein the stimulation generator is configured to deliver the symmetrical electrical stimulation via at least one segment electrode of the first group of segmented electrodes and at least one segment electrode of the second group of segmented electrodes and sense the response to the symmetrical electrical stimulation via at least one other segment electrode of the first group of segmented electrodes and at least one other segment electrode the second group of segmented electrodes.

Example 18. The neuromodulation system of example 15, wherein the stimulation generator is configured to deliver the symmetrical electrical stimulation via at least two of a first segment electrode of the first group of segmented electrodes, a first segment electrode of the second group of segment electrodes, the first electrode or the second electrode and sense the response to the symmetrical electrical stimulation via a second segment electrode of the first group of segmented electrodes and a second segment electrode of the second group of segmented electrodes.

Example 19. The neuromodulation system of example 15, wherein symmetrical electrical stimulation comprises electrical stimulation of a first amplitude through a first segment electrode of the first group of segmented electrodes and a corresponding first segment electrode of the second group of segmented electrodes, electrical stimulation of a second amplitude through a second segment electrode of the first group of segmented electrodes and a corresponding second segment electrode of the second group of segmented electrodes, and electrical stimulation of a third amplitude through a third segment electrode of the first group of segmented electrodes and a corresponding third segment electrode of the second group of segmented electrodes.

Example 20. The neuromodulation system of example 19, wherein at least one of the first amplitude, the second amplitude, or the third amplitude is 0.

Example 21. The neuromodulation system of any combination of examples 15-20, wherein the stimulation generator is configured to deliver the symmetrical electrical stimulation via one of current or voltage.

Example 22. The neuromodulation system of example 15 or example 21, wherein symmetrical electrical stimulation comprises for each electrical stimulation amplitude of each segment electrode of the first group of segmented electrodes, a matching electrical stimulation amplitude for one segment electrode of the second group of segmented electrodes.

Example 23. The neuromodulation system of example 15 or example 21, wherein symmetrical electrical stimulation comprises a total amplitude of electrical stimulation for each segment electrode of the first group segmented electrodes equaling a total amplitude of electrical stimulation for each segment electrode of the second group of segmented electrodes.

Example 24. The neuromodulation system of any of examples 15, or 19-23, wherein the first group of segmented electrodes and the second group of segmented electrodes are configured to deliver the symmetrical stimulation via different segment electrodes over time.

Example 25. The neuromodulation system of any of examples 15-24, wherein the adaptive neuromodulation system comprises an adaptive deep brain stimulation system.

Example 26. The neuromodulation system of any of examples 15-25, further comprising: a lead, wherein the lead comprises the first group of segmented electrodes, the second group of segmented electrodes, the first sensing electrode, and the second sensing electrode.

Example 27. A method of providing neuromodulation comprising: generating a symmetrical electrical stimulation signal; delivering the symmetrical electrical stimulation signal through at least one of a first electrode, a second electrode, at least one segment electrode of a first group of segmented electrodes or at least one segment electrode of a second group of segmented electrodes to a patient; sensing a response to the symmetrical electrical stimulation signal through at least two of the first electrode, the second sensing electrode, at least one other segment electrode of a first group of segmented electrodes or at least one other segment electrode of a second group of segmented electrodes; and adjusting at least one stimulation parameter of the symmetrical electrical stimulation signal based on the sensed response.

Example 28. The method of example 27, wherein the delivering the symmetrical electrical stimulation is via at least one segment electrode of the second group of segmented electrodes and the sensing the response to the symmetrical electrical stimulation is via the first electrode and the first group of segmented electrodes.

Example 29. The method of example 27, wherein the delivering the symmetrical electrical stimulation is via at least one segment electrode of the first group of segmented electrodes and at least one segment electrode of the second group of segmented electrodes and the sensing the response to the symmetrical electrical stimulation is via at least one other segment electrode of the first group of segmented electrodes and at least one other segment electrode the second group of segmented electrodes.

Example 30. The method of example 27, wherein the delivering the symmetrical electrical stimulation is via at least two of a first segment electrode of the first group of segmented electrodes, a first segment electrode of the second group of segment electrodes, the first electrode or the second electrode and the sensing the response to the symmetrical electrical stimulation via a second segment electrode of the first group of segmented electrodes and a second segment electrode of the second group of segmented electrodes.

Example 31. The method of example 27, wherein symmetrical electrical stimulation signal comprises electrical stimulation of a first amplitude through a first segment electrode of the first group of segmented electrodes and a corresponding first segment electrode of the second group of segmented electrodes, electrical stimulation of a second amplitude through a second segment electrode of the first group of segmented electrodes and a corresponding second segment electrode of the second group of segmented electrodes, and electrical stimulation of a third amplitude through a third segment electrode of the first group of segmented electrodes and a corresponding third segment electrode of the second group of segmented electrodes.

Example 32. The method of example 31, wherein at least one of the first amplitude, the second amplitude, or the third amplitude is 0.

Example 33. The method of any combination of examples 27-32, wherein the delivering the symmetrical electrical stimulation via one of current or voltage.

Example 34. The method of example 27 or example 33, wherein symmetrical electrical stimulation comprises for each electrical stimulation amplitude of each segment electrode of the first group of segmented electrodes, a matching electrical stimulation amplitude for one segment electrode of the second group of segmented electrodes.

Example 35. The method of example 27 or example 33, wherein symmetrical electrical stimulation comprises a total amplitude of electrical stimulation for each segment electrode of the first group of segmented electrodes equaling a total amplitude of electrical stimulation for each segment electrode of the second group of segmented electrodes.

Example 36. The method of any of examples 27, or 31-35, wherein the first group of segmented electrodes and the second group of segmented electrodes are configured to deliver the symmetrical stimulation over different segment electrodes over time.

Example 37. A non-transitory storage medium storing instructions, which, when executed, cause processing circuitry to: control a stimulation generator to generate a symmetrical electrical stimulation signal; control the stimulation generator to deliver the symmetrical electrical stimulation signal through at least one of a first electrode, a second electrode, at least one segment electrode of a first group of segmented electrodes, or at least one segment electrode of a second group of segmented electrodes to a patient; sense a response to the symmetrical electrical stimulation signal through at least two of the first electrode, the second electrode, at least one other segment electrode of the first group of segmented electrodes, or at least one other segment electrode of the second group of segmented electrodes; and control the stimulation generator to adjust at least one stimulation parameter of the symmetrical electrical stimulation signal based on the sensed response.

Various aspects of the disclosure have been described. These and other aspects are within the scope of the following claims.

The invention claimed is:

1. A neuromodulation system comprising:
a stimulation generator configured to deliver symmetrical electrical stimulation through a plurality of stimulation electrodes, the plurality of stimulation electrodes comprising at least two of a first electrode, a second electrode, at least one segment electrode of a first group of segmented electrodes, or at least one segment electrode of a second group of segmented electrodes, wherein the symmetrical electrical stimulation comprises electrical stimulation of a same amplitude from each stimulation electrode of a respective pair of stimulation electrodes;
a sensing channel configured to sense a response to the symmetrical electrical stimulation through a plurality of sense electrodes, the plurality of sense electrodes comprising at least two of the first electrode, the second electrode, at least one other segment electrode of the first group of segmented electrodes, or at least one other segment electrode of the second group of segmented electrodes, each of the plurality of sense electrodes being different than each of the plurality of stimulation electrodes; and
processing circuitry configured to:
control the stimulation generator to deliver the symmetrical electrical stimulation;
determine a response to the symmetrical electrical stimulation via the sensing channel; and
adjust at least one stimulation parameter of the symmetrical electrical stimulation based on the sensed response.

2. The neuromodulation system of claim 1, wherein the stimulation generator is configured to deliver the symmetrical electrical stimulation via at least one segment electrode of the second group of segmented electrodes and sense the response to the symmetrical electrical stimulation via the first electrode and the first group of segmented electrodes.

3. The neuromodulation system of claim 1, wherein the stimulation generator is configured to deliver the symmetrical electrical stimulation via at least one segment electrode of the first group of segmented electrodes and at least one segment electrode of the second group of segmented electrodes and sense the response to the symmetrical electrical stimulation via at least one other segment electrode of the first group of segmented electrodes and at least one other segment electrode of the second group of segmented electrodes.

4. The neuromodulation system of claim 1, wherein the stimulation generator is configured to deliver the symmetrical electrical stimulation via at least two of a first segment electrode of the first group of segmented electrodes, a first segment electrode of the second group of segment electrodes, the first electrode or the second electrode and sense the response to the symmetrical electrical stimulation via a second segment electrode of the first group of segmented electrodes and a second segment electrode of the second group of segmented electrodes.

5. The neuromodulation system of claim 1, wherein symmetrical electrical stimulation comprises electrical stimulation of a first amplitude through a first segment electrode of the first group of segmented electrodes and a corresponding first segment electrode of the second group of segmented electrodes, electrical stimulation of a second amplitude through a second segment electrode of the first group of segmented electrodes and a corresponding second segment electrode of the second group of segmented electrodes, and electrical stimulation of a third amplitude through a third segment electrode of the first group of segmented electrodes and a corresponding third segment electrode of the second group of segmented electrodes.

6. The neuromodulation system of claim 1, wherein symmetrical electrical stimulation comprises for each electrical stimulation amplitude of each segment electrode of the first group of segmented electrodes, a matching electrical stimulation amplitude for one segment electrode of the second group of segmented electrodes.

7. The neuromodulation system of claim 1, wherein symmetrical electrical stimulation comprises a total amplitude of electrical stimulation for each segment electrode of the first group segmented electrodes equaling a total amplitude of electrical stimulation for each segment electrode of the second group of segmented electrodes.

8. The neuromodulation system of claims 1, wherein the first group of segmented electrodes and the second group of segmented electrodes are configured to deliver the symmetrical stimulation via different segment electrodes over time to move the symmetrical stimulation around a longitudinal axis of a lead comprising the first group of segmented electrodes and the second group of segmented electrodes.

9. The neuromodulation system of claim 1, wherein the neuromodulation system comprises an adaptive deep brain stimulation system.

10. The neuromodulation system of claim 1, further comprising:
a lead, wherein the lead comprises the first group of segmented electrodes, the second group of segmented electrodes, the first sensing electrode, and the second sensing electrode.

11. A method of providing neuromodulation comprising:
generating a symmetrical electrical stimulation signal, the symmetrical electrical stimulation comprising electrical stimulation of a same amplitude from each stimulation electrode of a respective pair of stimulation electrodes;

delivering the symmetrical electrical stimulation signal through a plurality of stimulation electrodes, the plurality of stimulation electrodes comprising at least two of a first electrode, a second electrode, at least one segment electrode of a first group of segmented electrodes or at least one segment electrode of a second group of segmented electrodes to a patient;

sensing a response to the symmetrical electrical stimulation signal through a plurality of sense electrodes, the plurality of sense electrodes comprising at least two of the first electrode, the second sensing electrode, at least one other segment electrode of a first group of segmented electrodes or at least one other segment electrode of a second group of segmented electrodes, each of the plurality of sense electrodes being different than each of the plurality of stimulation electrodes; and adjusting at least one stimulation parameter of the symmetrical electrical stimulation signal based on the sensed response.

12. The method of claim 11, wherein the delivering the symmetrical electrical stimulation is via at least one segment electrode of the second group of segmented electrodes and the sensing the response to the symmetrical electrical stimulation is via the first electrode and the first group of segmented electrodes.

13. The method of claim 11, wherein the delivering the symmetrical electrical stimulation is via at least one segment electrode of the first group of segmented electrodes and at least one segment electrode of the second group of segmented electrodes and the sensing the response to the symmetrical electrical stimulation is via at least one other segment electrode of the first group of segmented electrodes and at least one other segment electrode of the second group of segmented electrodes.

14. The method of claim 11, wherein the delivering the symmetrical electrical stimulation is via at least two of a first segment electrode of the first group of segmented electrodes, a first segment electrode of the second group of segment electrodes, the first electrode or the second electrode and the sensing the response to the symmetrical electrical stimulation via a second segment electrode of the first group of segmented electrodes and a second segment electrode of the second group of segmented electrodes.

15. The method of claim 11, wherein symmetrical electrical stimulation signal comprises electrical stimulation of a first amplitude through a first segment electrode of the first group of segmented electrodes and a corresponding first segment electrode of the second group of segmented electrodes, electrical stimulation of a second amplitude through a second segment electrode of the first group of segmented electrodes and a corresponding second segment electrode of the second group of segmented electrodes, and electrical stimulation of a third amplitude through a third segment electrode of the first group of segmented electrodes and a corresponding third segment electrode of the second group of segmented electrodes.

16. The method of claim 11, wherein symmetrical electrical stimulation comprises for each electrical stimulation amplitude of each segment electrode of the first group of segmented electrodes, a matching electrical stimulation amplitude for one segment electrode of the second group of segmented electrodes.

17. The method of claim 11, wherein symmetrical electrical stimulation comprises a total amplitude of electrical stimulation for each segment electrode of the first group of segmented electrodes equaling a total amplitude of electrical stimulation for each segment electrode of the second group of segmented electrodes.

18. The method of claim 11, wherein the first group of segmented electrodes and the second group of segmented electrodes are configured to deliver the symmetrical stimulation over different segment electrodes over time to move the symmetrical stimulation around a longitudinal axis of a lead comprising the first group of segmented electrodes and the second group of segmented electrodes.

19. A non-transitory storage medium storing instructions, which, when executed, cause processing circuitry to:

control a stimulation generator to generate a symmetrical electrical stimulation signal, the symmetrical electrical stimulation comprising electrical stimulation of a same amplitude from each stimulation electrode of a respective pair of stimulation electrodes;

control the stimulation generator to deliver the symmetrical electrical stimulation signal through a plurality of stimulation electrodes, the plurality of stimulation electrodes comprising at least two of a first electrode, a second electrode, at least one segment electrode of a first group of segmented electrodes, or at least one segment electrode of a second group of segmented electrodes to a patient;

sense a response to the symmetrical electrical stimulation signal through a plurality of sense electrodes, the plurality of sense electrodes comprising at least two of the first electrode, the second electrode, at least one other segment electrode of the first group of segmented electrodes, or at least one other segment electrode of the second group of segmented electrodes, each of the plurality of sense electrodes being different than each of the plurality of stimulation electrodes; and control the stimulation generator to adjust at least one stimulation parameter of the symmetrical electrical stimulation signal based on the sensed response.

20. The neuromodulation system of claim 1, wherein for each respective pair of stimulation electrodes, a first stimulation electrode is a same distance from a first sense electrode of a sense electrode pair as a second stimulation electrode is from a second sense electrode of the sense electrode pair.

* * * * *